United States Patent
Yu et al.

(10) Patent No.: US 10,801,939 B2
(45) Date of Patent: Oct. 13, 2020

(54) APPARATUS FOR MEASURING BLOOD COAGULATION DATA AND USE METHOD THEREOF, CONNECTION MEMBER AND SUPPORT

(71) Applicant: NEOTEK BIOSCIENCE CO., LTD., Suzhou, Jiangsu (CN)

(72) Inventors: Bangzhong Yu, Jiangsu (CN); Feng Jiang, Jiangsu (CN)

(73) Assignee: NEOTEK BIOSCIENCE CO., LTD., Suzhou, Jiangsu (CN)

( * ) Notice: Subject to any disclaimer, the term of this patent is extended or adjusted under 35 U.S.C. 154(b) by 0 days.

(21) Appl. No.: 16/097,570

(22) PCT Filed: May 2, 2017

(86) PCT No.: PCT/CN2017/082757
§ 371 (c)(1),
(2) Date: Oct. 29, 2018

(87) PCT Pub. No.: WO2017/186185
PCT Pub. Date: Nov. 2, 2017

(65) Prior Publication Data
US 2019/0072470 A1    Mar. 7, 2019

(30) Foreign Application Priority Data

Apr. 29, 2016  (CN) .......................... 2016 1 0278393
Apr. 29, 2016  (CN) .......................... 2016 2 0383166
(Continued)

(51) Int. Cl.
*G01N 11/14* (2006.01)
*G01N 33/48* (2006.01)
(Continued)

(52) U.S. Cl.
CPC ................ *G01N 11/14* (2013.01); *F16C 3/02* (2013.01); *G01N 1/44* (2013.01); *G01N 33/48* (2013.01); *G01N 33/86* (2013.01)

(58) Field of Classification Search
CPC ........ G01N 11/14; G01N 33/86; G01N 33/48; G01N 1/44; G01N 33/4905; F16C 3/02
See application file for complete search history.

(56) References Cited

U.S. PATENT DOCUMENTS 5,204,065 A * 4/1993 Floyd ...................... B01J 3/002
                                                            215/260
2010/0154520 A1    6/2010 Schubert et al.
(Continued)

FOREIGN PATENT DOCUMENTS

CN    104181311 A    12/2014
CN    104458503 A    3/2015
(Continued)

OTHER PUBLICATIONS

English machine translation for document CN104458503.*
(Continued)

*Primary Examiner* — Daniel S Larkin
*Assistant Examiner* — Anthony W Megna Fuentes
(74) *Attorney, Agent, or Firm* — Hamre, Schumann, Mueller & Larson, P.C.

(57) ABSTRACT

An apparatus for measuring blood coagulation data, and a use method, a connection member and a support (2101) thereof are disclosed. The apparatus for measuring blood coagulation data comprises: a blood cup support (101), a detachment mechanism (102), and a rotary shaft (103, 805). The blood cup support (101) is used for supporting a blood cup (207) that is not used and a lid (206) of the blood cup, driving, under a first driving force, the blood cup (207) that is not used and the lid (206) of the blood cup to ascend until
(Continued)

the lid (206) of the unused blood cup to be connected to the rotary shaft (103, 805), and driving, under a second driving force, a blood cup (207) that is used to descend; and the detachment mechanism (102) is used for separating, under the second driving force, the lid (206) of the used blood cup from the rotary shaft (103, 805). The method can reduce the labor intensity in blood coagulation data measurement.

7 Claims, 12 Drawing Sheets

(30) Foreign Application Priority Data

| May 24, 2016 | (CN) | 2016 1 0347497 |
|---|---|---|
| May 24, 2016 | (CN) | 2016 2 0477597 |
| Aug. 30, 2016 | (CN) | 2016 1 0755564 |
| Aug. 30, 2016 | (CN) | 2016 1 0755577 |
| Aug. 30, 2016 | (CN) | 2016 1 0755814 |

(51) Int. Cl.
*G01N 1/44* (2006.01)
*F16C 3/02* (2006.01)
*G01N 33/86* (2006.01)

(56) References Cited

U.S. PATENT DOCUMENTS

2013/0206362 A1* 8/2013 Li .................... H01L 21/67115
165/61
2016/0091516 A1   3/2016 Gorin et al.

FOREIGN PATENT DOCUMENTS

| CN | 104614539 A | 5/2015 |
|---|---|---|
| CN | 105092478 A | 11/2015 |
| CN | 105805176 A | 7/2016 |
| CN | 105807039 A | 7/2016 |
| CN | 105910882 A | 8/2016 |
| CN | 205749523 U | 11/2016 |
| CN | 205786052 U | 12/2016 |
| CN | 106370829 A | 2/2017 |
| CN | 106405063 A | 2/2017 |
| CN | 106438668 A | 2/2017 |
| WO | 0049402 | 8/2000 |

OTHER PUBLICATIONS

International Search Report issued for International Patent Application No. PCT/CN2017/082757, dated Jul. 27, 2017, 10 pages including English translation.
Extended European Search Report issued for European Patent Application No. 17788837.7, dated Jun. 15, 2020, 8 pages.

* cited by examiner

APPARATUS FOR MEASURING BLOOD COAGULATION DATA AND USE METHOD THEREOF, CONNECTION MEMBER AND SUPPORT

TECHNICAL FIELD

The present invention relates to the technical field of medical apparatuses, and in particular, to an apparatus for measuring blood coagulation data and a use method thereof, a connection member and a support.

BACKGROUND

An apparatus for measuring blood coagulation data, such as a thrombelastography device, is a medical device for measuring whether blood can coagulate normally. This device has been used more and more widely. For example, the blood coagulation data of a patient is usually measured using the thrombelastography device before a surgery, and whether the blood coagulation process of the patient is normal is determined according to the measured blood coagulation data. The surgery can be made for the patient only when the blood can coagulate normally. If there is an abnormality in the blood coagulation process, the patient's blood will not be able to coagulate normally during the surgery, resulting in difficulty in stopping bleeding, and it is likely to endanger the patient's life. However, the existing thrombelastography device requires a large amount of time for measurement personnel, resulting in relatively large labor intensity for measuring the blood coagulation data.

SUMMARY

Embodiments of the present invention provides an apparatus for measuring blood coagulation data and a use method thereof, a connection member and a support, which can reduce the labor intensity in the blood coagulation data measurement.

An apparatus for measuring blood coagulation data as provided by an embodiment of the present invention, in which blood to be measured is contained in a blood cup and a lid of the blood cup, comprises a support, a detachment mechanism, and a rotary shaft, wherein the blood cup support is used for supporting the blood cup that is not used and the lid of the blood cup, driving, under a first driving force, the blood cup that is not used and the lid of the blood cup to ascend until the lid of the unused blood cup is connected to the rotary shaft, and driving, under a second driving force, a blood cup that is used to descend; and the detachment mechanism is used for separating, under the second driving force, the lid of the used blood cup from the rotary shaft.

An embodiment of the present invention provides an apparatus for measuring blood coagulation data and a method for mounting and detaching a blood cup. The blood cup support may drive, under a first driving force, the blood cup that is not used and a lid of the blood cup to ascend until the lid of the blood cup is connected to the rotary shaft, and therefore, the ascending of the blood cup and the mounting of the lid of the blood cup are automatically completed before the blood coagulation data is measured. The blood cup support may drive, under a second driving force, the blood cup that is used to descend, the detachment mechanism may separate, under the second driving force, the lid of the used blood cup from the rotary shaft at the same time, and therefore the descending of the blood cup and the detachment of the lid of the blood cup are automatically completed after the blood coagulation data is measured. In this way, in the process of measuring the blood coagulation data, the apparatus for measuring the blood coagulation data automatically completes the ascending and descending of the blood cup as well as the mounting and detachment of the lid of the blood cup, instead of a manner of manual operation. Therefore, the labor intensity in blood coagulation data measurement is reduced.

BRIEF DESCRIPTION OF THE DRAWINGS

In order to more clearly illustrate the embodiments of the present invention or the technical solutions in the prior art, the drawings used in the embodiments or the prior art description will be briefly described below. Apparently, the drawings in the following description are some embodiments of the present invention. For those of ordinary skill in the art, other drawings may also be obtained according to these drawings, without paying creative work.

DETAILED DESCRIPTION

In order to make the objective, the technical solution and the advantages of the embodiments of the present invention clearer, the technical solutions in the embodiments of the present invention are clearly and completely described below with reference to the accompanying drawings in the embodiments of the present invention. It is apparent that the described embodiments are part of the embodiments of the present invention, rather than all of the embodiments. All other embodiments obtained by those of ordinary skill in the art based on the embodiments of the present invention without paying creative work should fall within the protection scope of the present invention.

Figure 1:
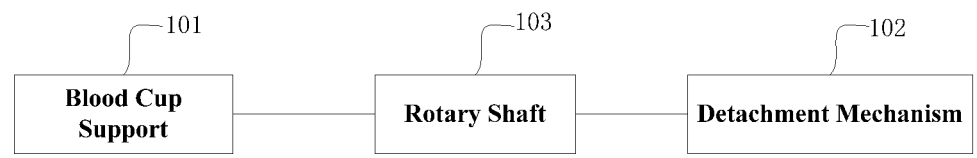
FIG. 1 is a schematic diagram of an apparatus for measuring blood coagulation data as provided by an embodiment of the present invention.

As shown in FIG. 1, an apparatus for measuring blood coagulation data as provided by an embodiment of the present invention, in which blood to be measured is contained in a blood cup and a lid of the blood cup, comprises a blood cup support 101, a detachment mechanism 102, and a rotary shaft 103, wherein the blood cup support 101 is used for supporting the blood cup that is not used and the lid of the blood cup, driving, under a first driving force, the blood cup that is not used and the lid of the blood cup to ascend until the lid of the unused blood cup is connected to the rotary shaft 103, and driving, under a second driving force, a blood cup that is used to descend; and the detachment mechanism 102 is used for separating, under the second driving force, the lid of the used blood cup from the rotary shaft 103.

An embodiment of the present invention provides an apparatus for measuring blood coagulation data. The blood cup support may drive, under a first driving force, the blood cup that is not used and a lid of the blood cup to ascend until the lid of the blood cup is connected to the rotary shaft, and therefore, the ascending of the blood cup and the mounting of the lid of the blood cup are automatically completed before the blood coagulation data is measured. The blood cup support may drive, under a second driving force, the blood cup that is used to descend, the detachment mechanism may separate, under the second driving force, the lid of the used blood cup from the rotary shaft at the same time, and therefore the descending of the blood cup and the detachment of the lid of the blood cup are automatically completed after the blood coagulation data is measured. In this way, in the process of measuring the blood coagulation data, the apparatus for measuring the blood coagulation data automatically completes the ascending and descending of the blood cup as well as the mounting and detachment of the lid of the blood cup, instead of a manner of manual operation. Therefore, the labor intensity in blood coagulation data measurement is reduced.

In an embodiment of the present invention, the blood cup may have a different shape, such as a cylindrical shape, a spherical shape provided with an opening, or the like.

In an embodiment of the present invention, the apparatus for measuring blood coagulation data further comprises a power source and a transmission mechanism, wherein the power source is used for supplying a driving force to the transmission mechanism; the transmission mechanism is used for applying the first driving force to the blood cup support under a driving force supplied by the power source, such that the lid of the blood cup is connected to the rotary shaft, and applying the second driving force to the blood cup support and the detachment mechanism, such that the lid of the blood cup is separated from the rotary shaft.

Figure 2:
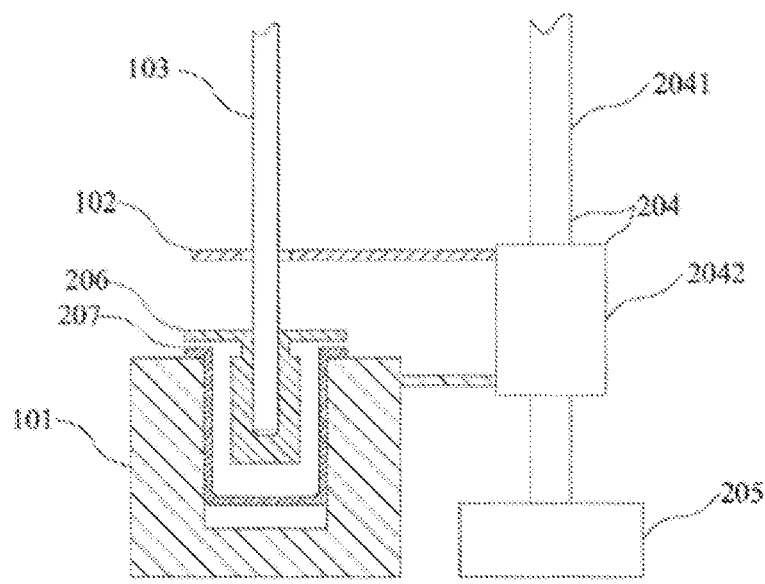
FIG. 2 is a state schematic diagram when the mounting of a blood cup is completed as provided by an embodiment of the present invention.

Specifically, the power source may be a stepping motor, and the transmission mechanism may be a screw. As shown in FIG. 2, the screw 204 comprises a screw rod 2041 and a nut 2042, wherein the screw rod 2041 is connected to the stepping motor 205, and the nut 2042 is connected to the blood cup support 101 and the detachment mechanism 102 respectively.

In an implementation manner, the detachment mechanism 102 is of a flaky structure provided with a through hole. The diameter of the rotary shaft is less than the diameter of the through hole in the detachment structure 102. The detachment mechanism 102 may be fixedly connected to the nut 2042 by welding, riveting, bonding, or the like. The blood cup support 101 is directly fixedly connected to the nut 2042, or is fixedly connected to the nut 2042 by means of a connection rod. The specific connection manner may be welding, riveting, bonding or bolting. Since the blood cup support 101 and the detachment mechanism 102 are both fixed on the nut 2042, in order to ensure that the blood cup 207 can be taken out from an opening in the upper end of the blood cup support 101, a distance between the opening in the upper end of the blood cup support 101 and the detachment mechanism 102 should be larger than the height of the blood cup 207.

In another implementation manner, the connection between the blood cup support 101 and the nut 2042 can keep the blood cup support 101 and the nut 2042 relatively stationary in a vertical direction, but the blood cup support 101 may rotate about the nut 2042 in a horizontal direction. In this way, when the blood cup 207 and the lid 206 of the blood cup need to be placed in the blood cup support 101, the blood cup support 101 rotates by a certain angle about the nut 2042, such that the opening in the upper end of the blood cup support 101 and the detachment mechanism 102 are staggered, and therefore the blood cup 207 and the lid 206 of the blood cup are placed in the blood cup support 101. Similarly, the detachment mechanism 102 and the nut 2042 remain relatively stationary in the vertical direction, and the detachment mechanism 102 may rotate about the nut 2042 in the horizontal direction, which can also achieve the above purpose. Of course, the detachment mechanism 102 and the blood cup support 101 may be connected to the nut 2042 by means of the above-described connection manner.

The screw rod 2041 can rotate forwardly or reversely under the driving force of the stepping motor 205. When the screw rod 2041 rotates forwardly, the nut 2042 moves upwards under the driving force of the screw rod 2041. Correspondingly, the nut 2041 applies a first driving force to the blood cup support 101 and the detachment mechanism 102, such that the blood cup support 101 and the detachment mechanism 102 move upwards. When the screw rod 2041 rotates reversely, the nut 2042 moves downwards under the driving force of the screw rod 2041. Correspondingly, the nut 2041 applies a second driving force to the blood cup support 101 and the detachment mechanism 102, such that the blood cup support 101 and the detachment mechanism 102 move downwards.

Figure 3:
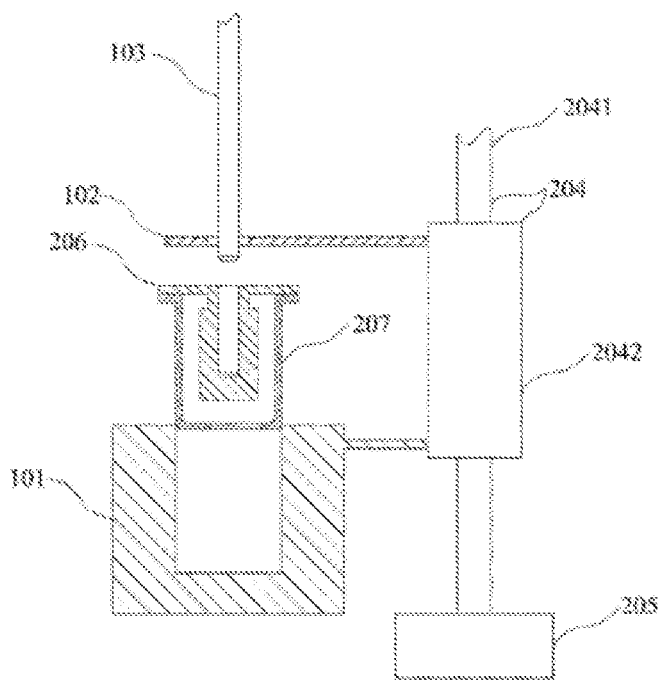
FIG. 3 is a state schematic diagram when the detachment of the blood cup is completed as provided by an embodiment of the present invention.

When the unused blood cup and the lid of the blood cup are placed on the blood cup support, the positions of the blood cup and the lid of the blood cup relative to the blood cup support are as shown in FIG. 3. When the stepping motor 205 drives the screw rod 2041 to rotate forwardly, the nut 2042 drives the blood cup support 101 and the detachment mechanism 102 to move upwards. After the blood cup support 101 moves upwards such that the lid 206 of the blood cup is in contact with the rotary shaft 103, the blood cup support 101 continues to move upwards. Since the position of the rotary shaft 103 is in a fixed state, the rotary shaft 103 enters into a mounting hole in the lid 206 of the blood cup. The rotary shaft 103 is connected to the lid 206 of the blood cup in an interference manner. When the end part of the rotary shaft 103 reaches the bottom of the mounting hole in the lid 206 of the blood cup, the blood cup support 101 continues to move upwards. The blood cup 207 enters the mounting hole in the blood cup support 101 under the action of the lid 206 of the blood cup until the upper edge of the blood cup 207 comes into contact with the blood cup support 101, and the stepping motor 205 stops rotating, such that the blood cup support 101 and the detachment mechanism 102 stop moving upwards. Then, the stepping motor 205 drives the screw rod 2041 to rotate reversely, so that the blood cup support 101 drives the blood cup 207 to move downwards. After a gap through which blood to be measured can be injected into the blood cup 207 appears between the blood cup 207 and the lid 206 of the blood cup, the stepping motor 205 stops rotating, waiting for the blood to be measured to be injected into the blood cup 207. After the blood to be measured is injected into the blood cup 207, the stepping motor 205 drives the screw rod 2041 to rotate forwardly to drive the blood cup 207 to ascend. The stepping motor 205 stops rotating when the distance between the blood cup 207 and the lid 206 of the blood cup reaches a set gap value. Then, the mounting of the blood cup 207 and the lid 206 of the blood cup is completed. The relative positional relationship between the blood cup 207 as well as the lid 206 of the blood cup and the blood cup support 101 is as shown in FIG. 2. In this case, the blood coagulation data of the blood to be measured can be measured by the rotary shaft 103.

In an embodiment of the present invention, as shown in FIG. 2 or FIG. 3, the detachment mechanism 102 is of a flaky structure provided with a through hole in the middle, wherein the diameter of the through hole is larger than the diameter of the rotary shaft 103, and the rotary shaft 103 passes through the through hole in the middle of the detachment mechanism 102, but is not in contact with the through hole.

After the blood coagulation data is measured, the relative positional relationship between the blood cup as well as the lid of the blood cup and the blood cup support is shown in FIG. 2. When the stepping motor 205 drives the screw rod 2041 to rotate reversely, the nut 2042 drives the blood cup support 101 and the detachment mechanism 102 to move downwards. Since the lid 206 of the blood cup is connected to the rotary shaft 103 in an interference manner, and the rotary shaft is in a fixed state in the vertical direction, when the blood cup support 101 moves downwards, the lid 206 of the blood cup is removed from the blood to be measured and separated from the blood cup 207, until the lid 206 of the blood cup is in contact with the detachment mechanism 102. After the lid 206 of the blood cup is in contact with the detachment mechanism 102, the stepping motor 205 continues to drive the screw rod 2041 to rotate reversely, such that the detachment mechanism 102 moves downwards. The detachment mechanism 102 moves downwards to drive the lid 206 of the blood cup to move downwards, and finally the lid 206 of the blood cup is removed from the rotary shaft 103, and the lid 206 of the blood cup, which is separated from the rotary shaft 103, falls into the blood cup 207. Then, the detachment of the lid 206 of the blood cup is completed.

In an embodiment of the present invention, as shown in FIG. 2 or FIG. 3, the blood cup support 101 has a cup-shaped structure. After the blood cup support 101 ascends by a certain distance under the first driving force and the lid 206 of the blood cup is completely connected to the rotary shaft 103, the lid 206 of the blood cup no longer moves under the action of the rotary shaft 103. However, the blood cup support 101 continues to ascend under the first driving force, the blood cup 207 enters the mounting hole in the blood cup support 101 in an interference manner under the action of the blood cup support 101 until the upper edge of the blood cup 207 is in contact with the blood cup support 101, and then the blood cup 207 is mounted in place.

Figure 4:
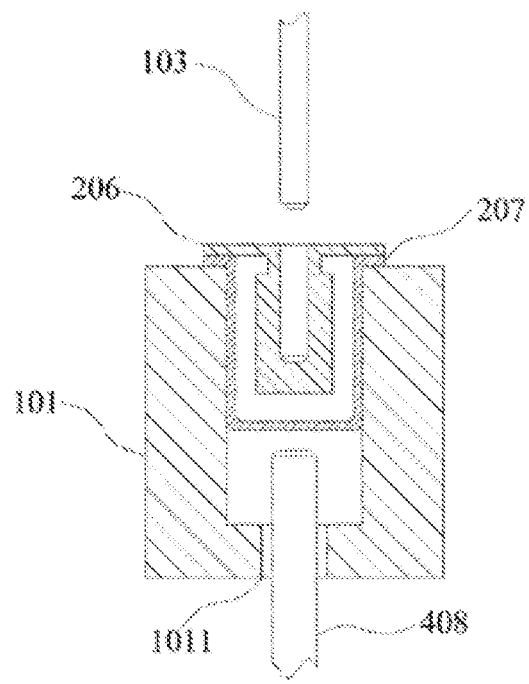
FIG. 4 is a schematic diagram of a blood cup support provided by an embodiment of the present invention.

In an embodiment of the present invention, as shown in FIG. 4, a through hole 1011 is formed in the bottom of the blood cup support 101. A thimble 408 which is fixedly arranged passes through the interior of the through hole 1011. After the lid 206 of the blood cup is separated from the rotary shaft 103, the lid 206 of the blood cup falls onto the blood cup 207. The blood cup support 101 continues to descend under the second driving force. The length of a part of the thimble 408, which ascends to enter the blood cup support 101, increases gradually. After the bottom of the blood cup 207 is in contact with the thimble 408, the blood cup 207 and the lid 206 of the blood cup move upwards, under the action of the thimble 408, relative to the blood cup support 101, until the blood cup 207 is completely removed from the blood cup support 101. The second driving force stops driving the blood cup support 101, and the blood cup support 101 stops moving. Then, the detachment of the blood cup 207 is completed.

In an embodiment of the present invention, the apparatus for measuring blood coagulation data further comprises a limiting mechanism. Since the rotary shaft will be subjected to certain thrust or pulling force when the lid of the blood cup and the blood cup are mounted or when the lid of the blood cup is detached, in order to prevent a bearing connected to the rotary shaft from being damaged by stress, the position of the rotary shaft is fixed by the limiting mechanism when the lid of the blood cup and the blood cup are mounted or when the lid of the blood cup is detached, such that the acting force encountered by the bearing connected to the rotary shaft is reduced. In this way, on the one hand, the bearing of the rotary shaft can be prevented from being damaged when the blood cup and the lid of the blood cup are mounted or detached; and on the other hand, the rotary shaft can be prevented from excessively deforming to affect the measurement accuracy of the blood coagulation data.

Specifically, the limiting mechanism may comprise pins. Correspondingly, a second support connected to the rotary shaft and a first support for supporting the second support are provided with at least one pin hole respectively. When the blood cup and the lid of the blood cup are mounted or detached, the pins are inserted into the pin holes in the first support and the second support to limit the relative positions of the first support and the second support, thereby fixing the position of the rotary shaft. Or, the limiting mechanism may comprise a pair of pliers. After the rotary shaft moves to a specific position, the pliers may grip the rotary shaft to fix the position of the rotary shaft.

Figure 5:
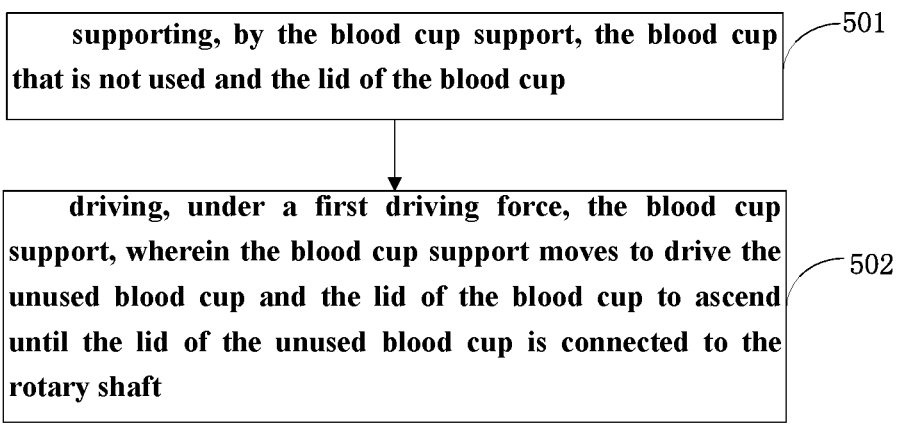
FIG. 5 is a flowchart of a method for mounting the blood cup as provided by an embodiment of the present invention.

As shown in FIG. 5, an embodiment of the present invention provides a method for mounting the blood cup based on any apparatus for measuring blood coagulation data as provided by the embodiment of the present invention. The method may comprise the following steps:

Operation 501: supporting, by the blood cup support, the blood cup that is not used and the lid of the blood cup;

Step 502: driving, under a first driving force, the blood cup support, wherein the blood cup support moves to drive the unused blood cup and the lid of the blood cup to ascend until the lid of the unused blood cup is connected to the rotary shaft.

In an embodiment of the present invention, the Step 502 includes: driving, by the first driving force, the blood cup support, wherein the blood cup support drives the unused blood cup and the lid of the blood cup to ascend until the lid of the unused blood cup continues to ascend by a set distance after contacting the rotary shaft and is then connected to the unused blood cup in an interference manner, such that the rotary shaft is connected to the lid of the unused blood cup in an interference manner.

Figure 6:
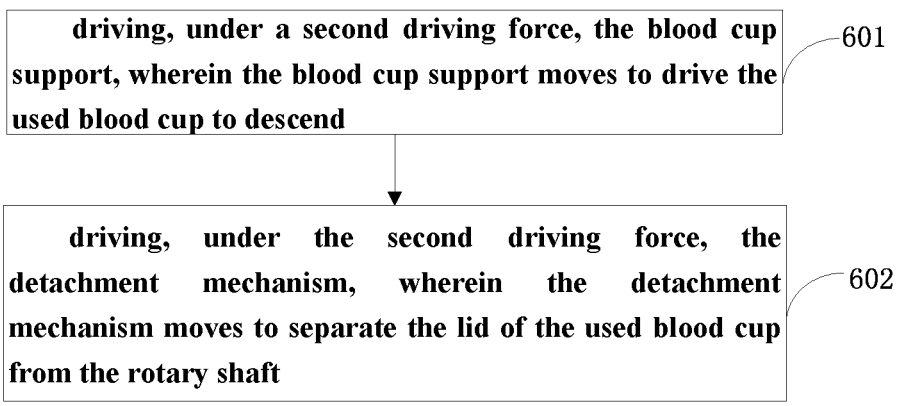
FIG. 6 is a flowchart of a method for detaching the blood cup as provided by an embodiment of the present invention.

As shown in FIG. 6, an embodiment of the present invention provides a method for detaching the blood cup based on any apparatus for measuring blood coagulation data as provided by the embodiment of the present invention. The method may comprise the following operations:

Operation 601: driving, under a second driving force, the blood cup support, wherein the blood cup support moves to drive the used blood cup to descend; and Operation 602: driving, under the second driving force, the detachment mechanism, wherein the detachment mechanism moves to separate the lid of the used blood cup from the rotary shaft.

In an embodiment of the present invention, the Operation 602 includes: driving, under the second driving force, the detachment mechanism to move towards the end part of the rotary shaft, wherein the detachment mechanism separates the lid of the used blood cup, which is connected to the end part of the rotary shaft in an interference manner, from the rotary shaft, and enabling the lid of the used blood cup, which is separated from the rotary shaft, to fall into the used blood cup.

In an embodiment of the present invention, when the apparatus for measuring blood coagulation data comprises a thimble, the operation 601 in which the blood cup support moves to drive the used blood cup to descend includes: after the blood cup support drives the used blood cup to descend by a set distance, the thimble is in contact with the bottom of the used blood cup, and separates the blood cup support and the used blood cup, which are connected in an interference manner, when the blood cup support continues to descend.

In order to more clearly illustrate the mounting method and the detachment method of the blood cup, the mounting method and the detachment method of the blood cup as provided by the embodiments will be further described in details by taking the entire measurement process of blood coagulation data as an example.

Figure 7:
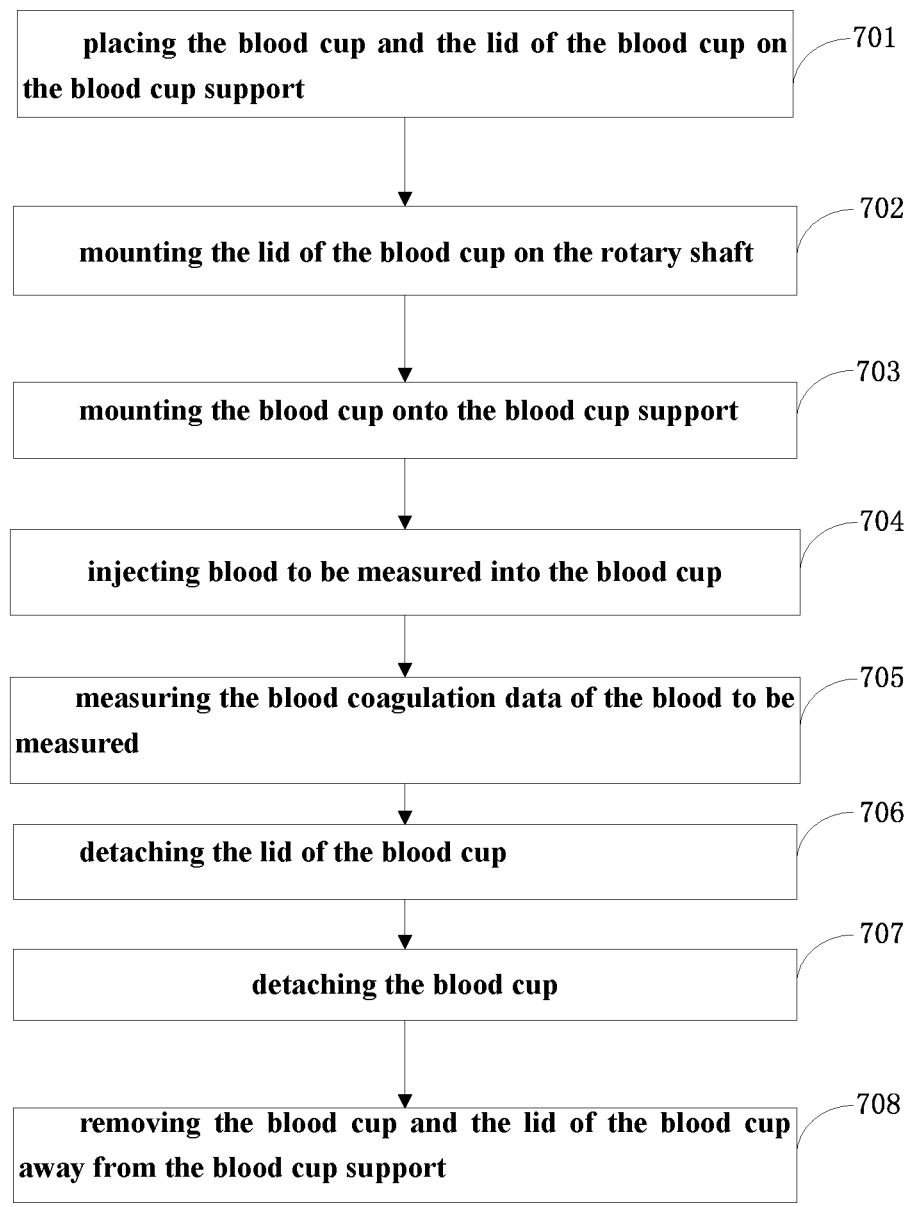
FIG. 7 is a flowchart of a method for mounting and detaching the blood cup as provided by an embodiment of the present invention.

As shown in FIG. 7, an embodiment of the present invention provides a method for measuring blood coagulation data. The method comprises the following operations 701-708.

Operation 701: placing the blood cup and the lid of the blood cup on the blood cup support.

In an embodiment of the present invention, when the blood coagulation data of blood to be measured needs to be measured, the lid of the unused blood cup covers the unused blood cup, and the blood cup with the lid is placed on the blood cup support.

As shown in FIG. 3, after the lid 206 of the blood cup covers the blood cup 207, the blood cup 207 with the lid 206 of the blood cup is placed on the blood cup support 101, wherein the bottom of the blood cup 207 is located at an opening of a mounting hole in the blood cup support 101.

Operation 702: mounting the lid of the blood cup on the rotary shaft.

In an embodiment of the present invention, the blood cup support is driven by a first driving force, such that the blood cup support ascends. The blood cup support ascends to drive the blood cup and the lid of the blood cup to ascend. After the lid of the blood cup is in contact with the rotary shaft, the blood cup support continues to drive the blood cup and the lid of the blood cup to ascend. The rotary shaft which is in a fixed state enters the mounting hole in the lid of the blood cup, such that the rotary shaft is connected to the lid of the blood cup in an interference manner. The blood cup support continues to ascend till the end part of the rotary shaft reaches the bottom of the mounting hole in the lid of the blood cup, thereby completing the mounting of the lid of the blood cup.

As shown in FIG. 3, a stepping motor 205 drives the screw rod 2041 to rotate forwardly, the screw rod 2041 rotates forwardly to drive the nut 2042 to ascend, and the blood cup support 101 moves upwards under the driving force of the nut 2042. The blood cup support 101 ascends to drive the blood cup 207 and the lid 206 of the blood cup to move upwards, till the end part of the rotary shaft 103 reaches the bottom of the mounting hole in the lid 206 of the blood cup, such that the lid 206 of the blood cup is connected to the rotary shaft 103 in an interference manner.

Operation 703: mounting the blood cup onto the blood cup support.

In an embodiment of the present invention, after the lid of the blood cup is mounted on the rotary shaft, the blood cup support continues to ascend under the first driving force. Since the lid of the blood cup cannot continue to move upwards under the action of the rotary shaft, the blood cup enters the mounting hole in the blood cup support under the actions of the lid of the blood cup and the blood cup support. The blood cup support continues to ascend till the upper edge of the blood cup is in contact with the blood cup support, and then the blood cup support stops moving. In this way, the blood cup is mounted on the blood cup support in an interference manner.

As shown in FIG. 3, after the lid 206 of the blood cup is mounted on the rotary shaft 103 in an inference manner, the lid 206 of the blood cup cannot continue to move upwards under the action of the rotary shaft 103. The stepping motor 205 continues to drive the blood cup support 101 to ascend. The blood cup 207 enters the mounting hole in the blood cup support 101 under the combined action of the blood cup support 101 and the lid 206 of the blood cup, till the upper edge of the blood cup 207 is in contact with the blood cup support 101. Then, the stepping motor 205 stops rotating, thereby completing the mounting of the blood cup 207.

Operation 704: injecting blood to be measured into the blood cup.

In an embodiment of the present invention, after the lid of the blood cup and the blood cup are mounted, the blood cup support is driven under the second driving force, such that the blood cup support drives the blood cup to move downwards by a certain distance, and therefore a gap through which the blood to be measured can be injected into the blood cup is formed between the blood cup and the lid of the blood cup. The blood to be measured and a corresponding reagent can be added into the blood cup through the gap between the blood cup and the lid of the blood cup. The blood cup support is driven under the first driving force to ascend, and the blood cup is driven by the blood cup support to ascend, and then stops moving till the gap between the blood cup and the lid of the blood cup reaches a preset value. Then, the positions of the blood cup and the lid of the blood cup have reached a measurement position.

As shown in FIG. 3, after the blood cup 207 is mounted on the blood cup support 101, the stepping motor 205 drives the screw rod 2041 to rotate reversely, such that the nut 2042 drives the blood cup support 101 to move downwards by a certain distance, for example, 10 mm; in this case, a gap having a width of 10 mm is formed between the blood cup 207 and the lid 206 of the blood cup, and the blood to be measured and the corresponding reagent are injected into the blood cup 207 through this gap. Then, the stepping motor 205 drives the screw rod 2041 to rotate forwardly, such that the nut 2042 drives the blood cup support 101 to move upwards by a certain distance, for example, move upwards by 5 mm; in this case, a gap of 5 mm remains between the blood cup 207 and the lid 206 of the blood cup, reaching the state shown in FIG. 2. In this case, the positions of the blood cup 207 and the lid 206 of the blood cup have reached the measurement position, and it is possible to begin to measure the blood coagulation data of the blood to be measured.

Operation 705: measuring the blood coagulation data of the blood to be measured.

In an embodiment of the present invention, as shown in FIG. 2, the blood cup 207 is driven by the blood cup support 101 to alternately rotate the blood cup 207 clockwise and counterclockwise. The blood in the blood cup 207 drives the lid 206 of the blood cup and the rotary shaft 103 to rotate in the corresponding directions, and the blood coagulation data of the blood to be measured is obtained according to the rotation angle of the rotary shaft 103.

Operation 706: detaching the lid of the blood cup.

In an embodiment of the present invention, after the blood coagulation data of the blood to be measured is measured, the detachment mechanism is driven to descend under the second driving force. Since the lid of the blood cup is connected to the rotary shaft, the detachment mechanism applies a downward acting force to the lid of the blood cup during the descending process, and the lid of the blood cup is driven to move downwards under the driving force of the detachment mechanism, and finally removed from the rotary shaft; the lid of the blood cup, which is separated from the rotary shaft, falls into the blood cup.

As shown in FIG. 2, after the blood coagulation data of the blood to be measured is measured, the stepping motor 205 drives the screw rod 2041 to rotate reversely, so that the nut 2042 drives the blood cup support 101 and the detachment mechanism 102 to move downwards. The detachment mechanism 102 comes into contact with the lid 206 of the blood cup after descending by a certain distance, and then continues to descend to push the lid 206 of the blood cup to move downwards until the lid 206 of the blood cup is removed from the rotary shaft 103. The lid 206 of the blood cup, which is separated from the rotary shaft 103, falls into the blood cup 207, thereby completing the detachment of the lid 206 of the blood cup.

Operation 707: detaching the blood cup.

In an embodiment of the present invention, the blood cup support continues to move downwards under the second driving force. When the thimble that ascends from the through hole in the bottom of the blood cup support comes into contact with the bottom of the blood cup, the thimble ejects the blood cup out from the mounting hole in the blood cup support as the blood cup support descends, thereby completing the detachment of the blood cup.

As shown in FIG. 4, the blood cup support 101 continues to descend under the driving force of the nut. After the blood cup support 101 descends by a certain distance, the bottom of the blood cup 207 comes into contact with the thimble 408 extending from the through hole 1011. As the blood cup support 101 continues to descend, the thimble 408 ejects the blood cup 207 out from the mounting hole in the blood cup support 101, thereby completing the detachment of the blood cup 207.

Operation 708: removing the blood cup and the lid of the blood cup away from the blood cup support.

In an embodiment of the present invention, after the blood cup and the lid of the blood cup are detached, the lid of the blood cup is separated from the rotary shaft. There is also no tight connection between the blood cup and the blood cup support, such that the blood cup and the lid of the blood cup are directly removed away from the blood cup support, thereby completing the blood coagulation data measurement.

It should be noted that, in the embodiment of the method of the present invention, the unused and used blood cups and the lids of the blood cups are collectively referred to as a blood cup and a lid of the blood cup, wherein the unused blood cup and the lid of the blood cup refer to the blood cup and the lid of the blood cup before the blood coagulation data is measured, and the used blood cup and the lid of the blood cup refer to the blood cup and the lid of the blood cup after the blood coagulation data of the blood to be measured is measured.

Figure 8:
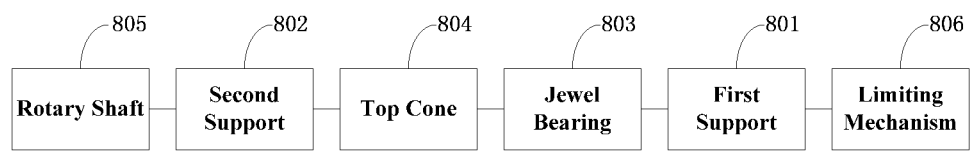
FIG. 8 is a schematic diagram of an apparatus for measuring blood coagulation data as provided by another embodiment of the present invention.

As shown in FIG. 8, an embodiment of the present invention provides an apparatus for measuring blood coagulation data, which comprises a first support 801, a second support 802, a jewel bearing 803, a top cone 804, a rotary shaft 805 and a limiting mechanism 806, wherein the first support 801 is connected to the jewel bearing 803, and the second support 802 is connected to the top cone 804 and the rotary shaft 805 respectively;

the jewel bearing 803 is used for supporting the top cone 804, such that the second support 802 and the rotary shaft 805 are able to rotate under the driving force of the blood to be measured; and the limiting mechanism 806 is used for limiting the position of the first support 801 to separate the jewel bearing 803 from the top cone 804 when the lid of the external blood cup is connected to or separated from the rotary shaft 805.

According to the apparatus for measuring blood coagulation data provided by an embodiment of the present invention, the jewel bearing is connected to the first support, and the top cone and the rotary shaft are connected to the second support respectively, and the first support supports the second support and the rotary shaft by the jewel bearing and the top cone which are matched together. When it is necessary to connect the lid of the blood cup to the rotary shaft or to separate the lid of the blood cup from the rotary shaft, the positions of the jewel bearing and the top cone are limited by the limiting mechanism to separate the jewel bearing from the top cone, and then the lid of the blood cup is connected to the rotary shaft or separated from the rotary shaft. In this way, when the lid of the blood cup is connected to or separated from the rotary shaft, the jewel bearing is not in contact with the top cone, such that the force encountered by the rotary shaft cannot act on the jewel bearing to prevent the jewel bearing from being damaged when the lid of the blood cup is connected to or separated from the rotary shaft, thereby reducing the risk that the jewel bearing is damaged.

Figure 9:
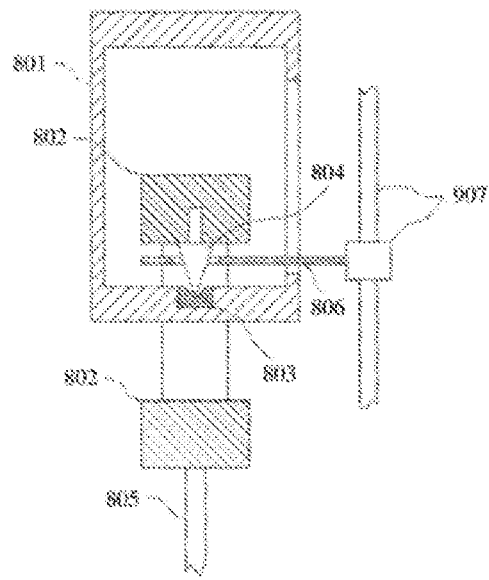
FIG. 9 is a schematic diagram of an apparatus device for measuring blood coagulation data, which is provided with a movable limiting mechanism, as provided by an embodiment of the present invention.

In an embodiment of the present invention, as shown in FIG. 9, the apparatus for measuring blood coagulation data may comprise a first driving mechanism 907. The first driving mechanism 907 is connected to the limiting mechanism 806; the first support 801 is connected to the jewel bearing 803, and the position of the first support 801 is fixed; the second support 802 is respectively connected to the top cone 804 and the rotary shaft 805; the jewel bearing 803 may support the top cone 804 in a vertical direction to rotate the rotary shaft 805 in the case of bearing less friction.

Figure 10:
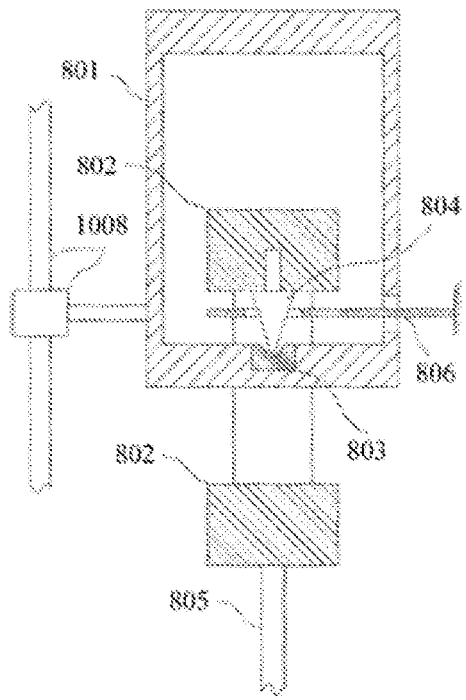
FIG. 10 is a schematic diagram of an apparatus for measuring blood coagulation data, which is provided with a fixed limiting mechanism, as provided by an embodiment of the present invention.

Specifically, the limiting mechanism 806 is of a flaky structure provided with a through hole. The diameter of the rotary shaft 805 is less than the diameter of the through hole in the limiting mechanism 806. When the limiting mechanism 806 may be driven by a driving mechanism to move, as shown in FIG. 9, the limiting mechanism 806 may be in contact with the second support 802 and drive the rotary shaft 805 to ascend, and stop moving after ascending by a certain distance to support the second support 802, thereby achieving the effect of fixing the position of the rotary shaft 805. Then, the rotary shaft 805 may be separated from the lid of the blood cup. When the limiting mechanism 806 is not able to move relatively under the driving mechanism, as shown in FIG. 10, the second support 802 is in contact with the limiting mechanism 806 after descending by a certain distance, and the second support 802 cannot continue to descend under the support of the limiting mechanism 806. Moreover, since the rotary shaft 805 is fixed to the second support 806, the limiting mechanism 806 can achieve the effect of fixing the position of the rotary shaft 805. Then, the rotary shaft 805 may be separated from the lid of the blood cup.

When the lid of the blood cup needs to be mounted on the rotary shaft 805 or removed from the rotary shaft 805, the first driving mechanism 907 drives the limiting mechanism 806. The limiting mechanism 806 drives the second support 802 to move upwards under the driving force of the first driving mechanism 907, and the second support 802 moves upwards to drive the top cone 804 and the rotary shaft 805 to move upwards, such that the jewel bearing connected to the first support 801 is separated from the top cone 804 connected to the second support 802. After the jewel bearing 803 is separated from the top cone 804, the limiting mechanism 806 supports the second support 802, the top cone 804 and the rotary shaft 805.

When the lid of the blood cup is mounted on the rotary shaft 805, the lid of the blood cup pushes the rotary shaft 805 to move upwards. The rotary shaft 805 moves upwards to drive the second support 802 and the top cone 804 to continue to ascend until the first support 801 is in direct contact with the second support 802. The second support 802 and the rotary shaft 805 stop moving under the action of the first support 801, and the lid of the blood cup continues to ascend and is connected to the rotary shaft in an interference manner. During the mounting process of the lid of the blood cup, the jewel bearing 803 does not come into contact with the top cone 804, thereby preventing the jewel bearing 803 from being damaged by the force or impact generated during the mounting process of the lid of the blood cup.

When the lid of the blood cup is removed from the rotary shaft 805, the lid of the blood cup is subjected to a downward acting force. Since the lid of the blood cup is connected to the rotary shaft 805 in an interference manner, the rotary shaft 805 is also subjected to a downward force. However, since the limiting mechanism 806 supports the second support 802, the top cone 804, and the rotary shaft 805, the rotary shaft 805 does not move. The lid of the blood cup is displaced relative to the rotary shaft 805 under the downward force, thereby achieving the effect of separating the lid of the blood cup from the rotary shaft 805. In the process of removing the lid of the blood cup from the rotary shaft 805, since the limiting mechanism 806 has driven the top cone 804 to be separated from the jewel bearing 803 in advance, the limiting mechanism 806 supports the second support 802 in the process of removing the lid of the blood cup from the rotary shaft 805. The relative positions of the jewel bearing 803 and the top cone 804 are not changed, so that the jewel bearing 803 does not come into contact with the top cone 804 in the process of removing the lid of the blood cup from the rotary shaft 805, thereby preventing the jewel bearing 803 from being damaged by an acting force or impact generated in the process of detaching the lid of the blood cup. The first driving mechanism 907 may be implemented by a screw.

In an embodiment of the present invention, as shown in FIG. 10, the apparatus for measuring blood coagulation data may comprise a second driving mechanism 1008. The second driving mechanism 1008 is connected to the first support 801. The limiting mechanism 806 is fixed relative to the first support 801 and the second support 802. The first support 801 is connected to the jewel bearing 803, and the position of the first support 801 is fixed. The second support 802 is connected to the top cone 804 and the rotary shaft 805 respectively. The jewel bearing 803 supports the top cone 804 in a vertical direction, such that the rotary shaft 805 rotates in a case of bearing less friction.

When the lid of the blood cup needs to be mounted on the rotary shaft 805 or removed from the rotary shaft 805, the second driving mechanism 1008 drives the first support 801, such that the first support 801 descends. When the first support 801 begins to descend, the second support 802 descends along with the first support 801. The second support 802 is in contact with the limiting mechanism 806 after descending by a certain distance, and the second support 802 stops descending under the support of the limiting mechanism 806. However, the first support 801 continues to descend under the action of the second driving mechanism 1008, so that the jewel bearing 803 is separated from the top cone 804. After the jewel bearing 803 is separated from the top cone 804, the second driving mechanism 1008 stops driving the first support 801 and supports the first support 801 to maintain the first support 801 at the current position.

When the lid of the blood cup is mounted on the rotary shaft 805, the lid of the blood cup is subjected to an upward acting force. Since the lid of the blood cup is connected to the rotary shaft 805 in an interference manner, the rotary shaft 805 is also subjected to an upward force from the lid of the blood cup when the lid of the blood cup is in contact with the rotary shaft 805. The rotary shaft 805 drives the second support 802 and the top cone 804 to move upwards under the upward force until the first support 801 is in direct contact with the second support 802. The first support 801 is in a fixed state under the support of the second driving mechanism 1008. After the second support 802 is in contact with the first support 801, the second support 802 and the rotary shaft 805 stop moving under the action of the first support 801. The lid of the blood cup moves relative to the rotary shaft 805 under the upward force, and is connected to the rotary shaft 805 in an interference manner, thereby completing the mounting of the lid of the blood cup. Since the second driving device 1008 has driven the first support 801 to move to separate the jewel bearing 803 from the top cone 804 before the lid of the blood cup is mounted, the second driving device 1008 supports the first support 801 in the process of mounting the lid of the blood cup, thereby ensuring that the position of the jewel bearing 803 is not changed. The second support 802 drives the top cone to move away from the jewel bearing 803 under the driving force of the rotary shaft 805, such that the jewel bearing 803 is not in contact with the top cone 804 in the process of mounting the lid of the blood cup, thereby preventing the jewel bearing 803 from being damaged by the acting force or impact generated in the process of mounting the lid of the blood cup.

When the lid of the blood cup is removed from the rotary shaft 805, the lid of the blood cup is subjected to a downward acting force. Since the lid of the blood cup is connected to the rotary shaft 805 in an interference manner, the rotary shaft 805 is also subjected to a downward force. However, since the second driving mechanism 1008 supports the first support 801, the position of the first support 801 is fixed, thereby ensuring that the position of the jewel bearing 803 is not changed. Meanwhile, the second support 802 is in a fixed state under the support of the limiting mechanism 806 to ensure that the position of the top cone 804 is not changed, thereby ensuring that the jewel bearing 803 is not in contact with the top cone 804. Since the rotary shaft 805 does not move under the support of the second driving mechanism 1008, the lid of the blood cup moves downwards relative to the rotary shaft 805 under the downward force, and is removed from the rotary shaft 805, thereby achieving the effect of separating the lid of the blood cup from the rotary shaft 805. Since the jewel bearing 803 is not in contact with the top cone 804 during the whole process of removing the lid of the blood cup, there is no acting force between the jewel bearing 803 and the top cone 804, thereby preventing the jewel bearing 803 from being damaged by the acting force or impact generated in the process of detaching the lid of the blood cup.

The second driving mechanism 1008 is implemented by a screw.

Figure 11:
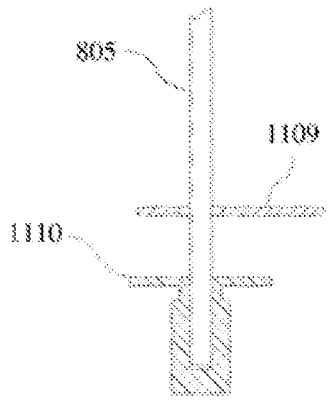
FIG. 11 is a schematic diagram of a detachment mechanism provided by an embodiment of the present invention.

In an embodiment of the present invention, the apparatus for measuring blood coagulation data may further comprise a detachment mechanism, wherein a through hole is formed in the middle of the detachment mechanism. The rotary shaft passes through the through hole in the middle of the detachment mechanism and is not in contact with the detachment mechanism. The detachment mechanism can move towards the end part of the rotary shaft under a driving force, and drive the lid of the blood cup, which is connected to the end part of the rotary shaft, to move relative to the rotary shaft, thereby detaching the lid of the blood cup from the rotary shaft, such that the lid of the blood cup is separated from the rotary shaft. In this way, the separation of the lid of the blood cup from the rotary shaft may be automatically completed by the detachment mechanism, without manual operation, thereby reducing the labor intensity of the measurement person during the blood coagulation data measurement As shown in FIG. 11, the lid of the blood cup 1110 is connected to the end part of the rotary shaft 805 in an interference manner. When the lid 110 of the blood cup needs to be separated from the rotary shaft 805, the detachment mechanism 1109 is driven under a driving force, such that the detachment mechanism 1109 moves downwards. When the detachment mechanism 1109 is in contact with the lid of the blood cup 1110, the lid 1110 of the blood cup is subjected to a downward acting force. However, the rotary shaft 805 is in a fixed state under the action of the second support, the lid 1110 of the blood cup moves downwards relative to the rotary shaft 805 under the downward acting force, such that the lid 1110 of the blood cup can be removed from the rotary shaft 805, thereby realizing the separation of the lid 1110 of the blood cup from the rotary shaft 805. The detachment mechanism 1109 may be driven by a device, such as a stepping motor, thereby realizing automatic separation of the lid 1110 of the blood cup from the rotary shaft 805. The lid of the blood cup may be separated from the rotary shaft, without manual operation, thereby reducing the labor intensity of measurement personnel during the blood coagulation data measurement.

Figure 12:
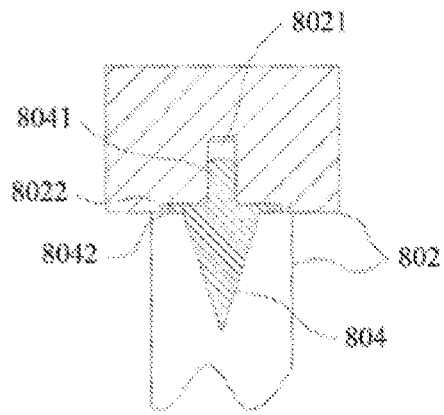
FIG. 12 is a schematic diagram of a top cone and a second support provided by an embodiment of the present invention.

In an embodiment of the present invention, as shown in FIG. 12, a connection bolt 8014 and a first guide platform 8042 are arranged on the top cone 804; a connection nut 8021 and a second guide platform 8022 are arranged on the second support 802; the connection bolt 8041 is matched with the connection nut 8021, such that the top cone 804 is connected to the second support 802. After the connection bolt 8041 is matched with the connection nut 8021, the first guide platform 8042 is attached to the second guide platform 8022, such that an included angle between the top cone 804 and the second support 802 is limited.

Since there is a certain gap between threaded connections, if the second support 802 is connected to the top cone 804 simply by a threaded connection, there is a certain error between the relative positions of the top cone 804 and the second support 802, such that the included angle between the top cone 804 and the second support 802 is not equal to 90°. When the included angle between the top cone 804 and the second support 802 is not equal to 90°, the axis of the rotary shaft supported by the top cone 804 will have a non-zero included angle with the vertical direction. In this way, the driving force and the frictional force, which are encountered by the rotary shaft, will change, resulting in a larger error in the blood coagulation data determined according to the rotation angle of the rotary shaft.

By providing the first guide platform 8042 and the second guide platform 8022, after the connection bolt 8041 is matched with the connection nut 8021, the first guide platform 8042 and the second guide platform 8022 are attached to each other. By performing finish machining on the first guide platform 8042 and the second guide platform 8022, the flatness of the first guide platform 8042 and the second guide platform 8022 is ensured. When the first guide platform 8042 and the second guide platform 8022 are attached to each other, the included angle between the top cone 804 and the second support 802 is ensured to be equal to 90°, so that the included angle between the axis of the rotary shaft and the vertical direction is zero. Therefore, the accuracy of measuring the blood coagulation data by the apparatus for measuring the blood coagulation data is ensured.

In an embodiment of the present invention, the apparatus for measuring blood coagulation data may further comprise a first magnet and a second magnet, wherein the first magnet is connected to the first support, and the second magnet is connected to the second support; and the positions of the first magnet and the second magnet correspond to each other, and like magnetic poles of the first magnet and the second magnet are opposite. Since the positions of the first magnet and the second magnet correspond to each other, and like magnetic poles of the first magnet and the second magnet are opposite, a repulsive force will be generated between the first magnet and the second magnet, and the repulsive force will reduce the pressure of the top cone on the jewel bearing. When the pressure of the top cone on the jewel bearing is reduced, the frictional force between the top cone and the jewel bearing can be reduced. As the frictional force between the top cone and the jewel bearing is reduced, the resistance encountered during the rotation of the rotary shaft may be reduced. The rotation angle of the rotary shaft can more accurately reflect the viscosity of the blood to be measured, thereby further improving the accuracy of measuring the blood coagulation data by the apparatus for measuring blood coagulation data.

It should be noted that the apparatus for measuring blood coagulation data provided by the embodiment of the present invention can realize the separation of the jewel bearing from the top cone, thereby preventing the jewel bearing or the top cone from being damaged. The separation process may occur during the mounting and detaching process of the lid of the blood cup or during the process of transporting the apparatus for measuring the blood coagulation data, thereby preventing the jewel bearing or the top cone from being damaged by the shaking of the rotary shaft in the process of transporting the apparatus for measuring blood coagulation data, and generally improving the safety of the apparatus for measuring blood coagulation data.

Figure 13:
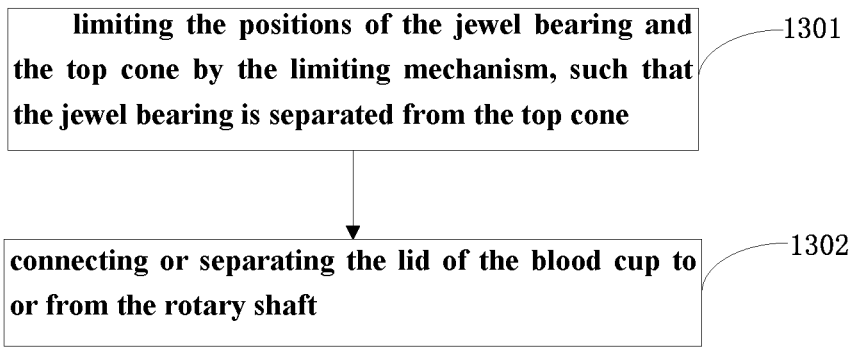
FIG. 13 is a flowchart of a method for detaching a lid of the blood cup as provided by an embodiment of the present invention.

As shown in FIG. 13, an embodiment of the present invention provides a method for mounting and detaching the lid of the blood cup based on any apparatus for measuring blood coagulation data provided by the embodiment of the present invention, comprising the following operations:

Operation 1301: limiting the positions of the jewel bearing and the top cone by the limiting mechanism, such that the jewel bearing is separated from the top cone; and Operation 1302: connecting or separating the lid of the blood cup to or from the rotary shaft.

In an embodiment of the present invention, when the apparatus for measuring blood coagulation data comprises a first driving mechanism, the operation of limiting the position of the first support by the limiting mechanism, such that the jewel bearing is separated from the top cone includes:

driving, by the first driving mechanism, the limiting mechanism, such that the limiting mechanism drives the first support to move, and then the jewel bearing is separated from the top cone; and after the jewel bearing is separated from the top cone, further including:

supporting the first support by the limiting mechanism.

In an embodiment of the present invention, when the apparatus for measuring blood coagulation data comprises a second driving mechanism, the operation of limiting the position of the first support by the limiting mechanism, such that the jewel bearing is separated from the top cone includes:

driving the first support by the second driving mechanism, such that the first support descends; limiting the position of the second support by the limiting mechanism when the first support descends, such that the jewel bearing is separated from the top cone; and after the jewel bearing is separated from the top cone, further including:

supporting the first support by the second driving mechanism.

In an embodiment of the present invention, when the apparatus for measuring the blood coagulation data comprises the detachment mechanism, the operation of separating the lid of the blood cup from the rotary shaft includes:

moving, under a driving force, the detachment mechanism to move towards the end part of the rotary shaft, such that the detachment mechanism drives the lid of the blood cup, which is connected to the end part of the rotary shaft, to move relative to the rotary shaft, the lid of the blood cup is removed from the rotary shaft, and then the lid of the blood cup is separated from the rotary shaft.

In order to make the methods for mounting and detaching the lid of the blood cup provided by the present invention more clear, the methods for mounting and detaching the lid of the blood cup will be further described in detail below with reference to the apparatus for measuring blood coagulation data shown in FIGS. 2 and 3.

Figure 14:
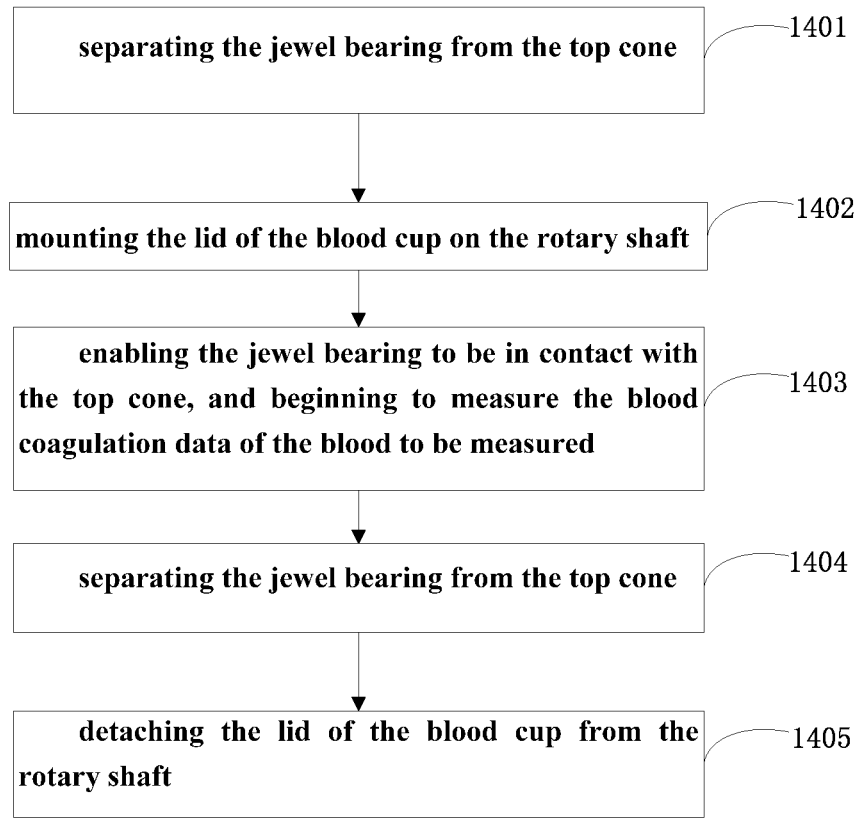
FIG. 14 is a flowchart of a method for detaching the lid of the blood cup as provided by another embodiment of the present invention.

As shown in FIG. 14, an embodiment of the present invention provides a method for mounting and detaching the lid of the blood cup. The method comprises the following operations 1401-1405.

Operation 1401: separating the jewel bearing from the top cone.

In an embodiment of the present invention, before the lid of the blood cup is mounted, the positions of the jewel bearing and the top cone are limited by the limiting mechanism first, such that the jewel bearing is separated from the top cone, thereby preventing the jewel bearing and the top cone from being damaged in the process of mounting the lid of the blood cup.

For example, as shown in FIG. 9, before the lid of the blood cup is connected to the rotary shaft 805, the limiting mechanism 806 is driven by the first driving mechanism 207, such that the limiting mechanism 806 ascends. The limiting mechanism 806 ascends to drive the second support 802, the top cone 804 and the rotary shaft 805 to ascend, such that the jewel bearing 803 is separated from the top cone 804. The limiting mechanism 806 stops moving after ascending by a certain distance to support the second support 802, the top cone 804 and the rotary shaft 805.

For example, as shown in FIG. 10, before the lid of the blood cup is connected to the rotary shaft 805, the first support 801 is driven by the second driving mechanism 308, such that the first support 801 descends. When the first support 801 begins to descend, the second support 802 descends along with the first support 801. The second support 802 is in contact with the fixed limiting mechanism 806 after descending by a certain distance. The second support 802 stops descending under the support of the limiting mechanism 806. However, the first support 801 continues to descend under the action of the second driving mechanism 1008, such that the jewel bearing 803 is separated from the top cone 804. After the jewel bearing 803 is separated from the top cone 804, the first support 801 stops moving after continuing to descend by a certain distance. The second driving mechanism 1008 supports the first support 801 and the jewel bearing 803. The limiting mechanism 806 supports the second support 802, the top cone 804 and the rotary shaft 805.

Operation 1402: mounting the lid of the blood cup on the rotary shaft.

In an embodiment of the present invention, after the jewel bearing is separated from the top cone, the mounting hole in the lid of the blood cup is in contact with the end part of the rotary shaft. An upward acting force is applied to the lid of the blood cup, and the lid of the blood cup moves relative to the rotary shaft under this acting force, so that the end part of the rotary shaft enters the mounting hole in the lid of the blood cup, and the lid of the blood cup is connected to the rotary shaft in an interference manner.

For example, as shown in FIG. 9 or 10, after the jewel bearing 803 is separated from the top cone 804, the mounting hole in the lid of the blood cup is in contact with the tip at the lower part of the rotary shaft 805. An upward acting force is applied to the lid of the blood cup and is transmitted to the rotary shaft 805 by means of the lid of the blood cup. The rotary shaft 805 drives the second support 802 and the top cone 804 to move upwards under the acting force until the second support 802 is in direct contact with the fixed first support 801. After the second support 802 is in contact with the first support 801, the second support 802 and the rotary shaft 805 cannot continue to move upwards under the action of the first support 801. In this case, the lid of the blood cup moves relative to the rotary shaft 805 under the upward acting force. The lower end of the rotary shaft 805 enters the mounting hole in the lid of the blood cup, and the rotary shaft 805 is connected to the lid of the blood cup in an interference manner.

Operation 1403: enabling the jewel bearing to be in contact with the top cone, and beginning to measure the blood coagulation data of the blood to be measured.

In an embodiment of the present invention, after the lid of the blood cup is mounted on the rotary shaft, the positions of the jewel bearing and the top cone are limited again by the limiting mechanism, such that the jewel bearing is in contact with the top cone. The second support and the rotary shaft are supported by the top cone. The lid of the blood cup is placed on the blood cup. The lid of the blood cup drives, under the driving force of the blood to be measured, the rotary shaft to rotate. The blood coagulation data of the blood to be measured is obtained according to the rotation angle of the rotary shaft.

For example, as shown in FIG. 9, before the lid of the blood cup is connected to the rotary shaft 805, the limiting mechanism 806 is driven by the first driving mechanism 907, such that the limiting mechanism 806 descends. As the limiting mechanism 806 descends, the second support 802, the top cone 804 and the rotary shaft 805 descend together with the limiting mechanism 806. After the top cone 804 is in contact with the jewel bearing 803, the limiting mechanism 806 continues to descend by a certain distance to be separated from the second support 802. After the limiting mechanism 806 is separated from the second support 802, the second support 802 and the rotary shaft 805 are supported by the top cone 804. The lid of the blood cup, the rotary shaft 805 and the second support 802 rotate under the driving force of the blood to be measured. The blood coagulation data of the blood to be measured is determined according to the rotation angle of the rotary shaft 805.

For example, as shown in FIG. 10, after the lid of the blood cup is connected to the rotary shaft 805, the first support 801 is driven by the second driving mechanism 1008, such that the first support 801 and the jewel bearing 803 ascend. After the jewel bearing 803 is in contact with the top cone 804, the second driving mechanism 1008 drives the first support 801 to continue to ascend by a certain distance, such that the second support 802 is separated from the limiting mechanism 806. After the second support 802 is separated from the limiting mechanism 806, the second driving mechanism 1008 steps moving to support the first support 801, and the first support 801 supports the second support 802 and the rotary shaft 805 by means of the jewel bearing 803 and the top cone 804. The lid of the blood cup, the rotary shaft 805 and the second support 802 rotate under the driving force of the blood to be measured. The blood coagulation data of the blood to be measured is determined according to the rotation angle of the rotary shaft 805.

Operation 1404: separating the jewel bearing from the top cone.

In an embodiment of the present invention, after the blood coagulation data of the blood to be measured is measured, it is necessary to detach the lid of the used blood cup from the rotary shaft. Before the lid of the blood cup is detached, it is necessary to separate the jewel bearing from the top cone first. Specifically, the process of separating the jewel bearing from the top cone is same as the Operation 1401, and will not be repeated here again.

Operation 1405: detaching the lid of the blood cup from the rotary shaft.

In an embodiment of the present invention, after the jewel bearing is separated from the top cone. The lid of the blood cup is pushed by the detachment mechanism to move on the rotary shaft, such that the lid of the blood cup is detached from the rotary shaft, and then the lid of the blood cup is separated from the rotary shaft.

For example, as shown in FIG. 11, the detachment mechanism 1109 is driven under a driving force, such that the detachment mechanism 1109 moves downwards. The detachment mechanism 1109 moves downwards to apply a downward acting force on the lid of the blood cup after contacting the lid 1110 of the blood cup. The lid 110 of the blood cup moves downwards under this downward acting force. When the lid 1110 of the blood cup moves downwards, the rotary shaft 805 is in a fixed state. The lid 1110 of the blood cup moves downwards by a distance and is then pushed away from the rotary shaft 805 to realize separation of the lid 1110 of the blood cup from the rotary shaft 805.

As shown in FIG. 9 or 10, when the lid of the blood cup is subjected to a downward acting force, the rotary shaft 805, the second support 802 and the top cone 804 are in a fixed state under the support of the limiting mechanism 806. Since the rotary shaft 805 cannot move downwards, the lid of the blood cup is driven by the downward acting force to move relative to the rotary shaft 805, and the lid of the blood cup is removed from the rotary shaft, so that the lid of the blood cup and the rotary shaft which are connected in an interference manner are separated. As the lid of the blood cup and the rotary shaft are separated, the position of the first support 801 is fixed. The second support 802 resists a downward pulling force from the rotary shaft by means of the limiting mechanism 806, and the jewel bearing 803 is not in contact with the top cone 804 and has no interaction force with the top cone, so that the jewel bearing 803 and the top cone 804 cannot be damaged when the lid of the blood cup is separated from the rotary shaft.

Figure 15:
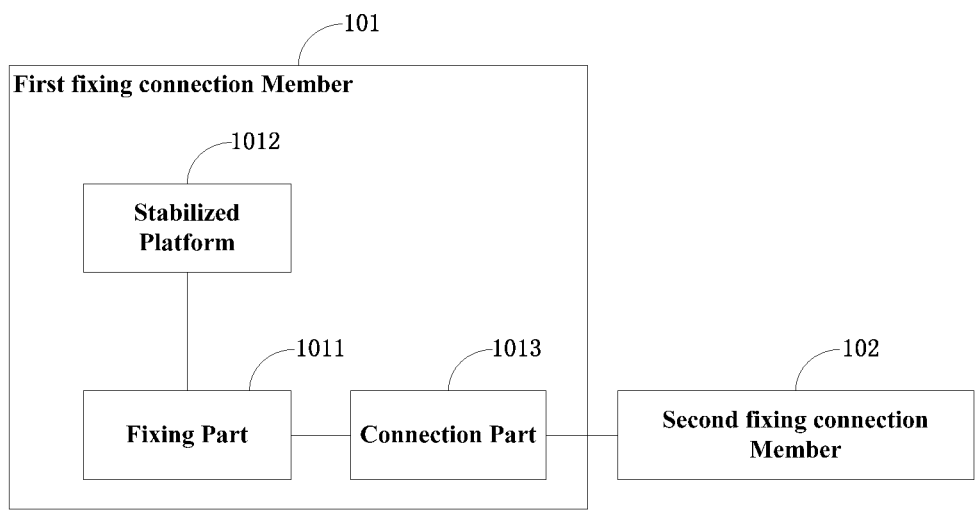
FIG. 15 is a structural schematic diagram of a connection assembly provided by an embodiment of the present invention.

As shown in FIG. 15, an embodiment of the present invention provides a connection assembly. The connection assembly comprises a first fixing connection member 1501 and a second fixing connection member 1502, wherein the first fixing connection member comprises a fixing part 15011, a stabilized platform 15012 fixed on the fixing part 15011, and a connection part 15013 fixed on the fixing part 15011, wherein the fixing part 15011 is fixed to an external first support assembly;

the stabilized platform 15012 is attached to a plane of the external first support assembly;

the connection part 15013 and the second fixing connection member 1502 are connected together in a form of point connection;

the second fixing connection member 1502 is fixedly connected to an external second support assembly; and the external first support assembly rotates, under an external power, relative to the external second support assembly by means of the point connection of the connection part 15013 and the second fixing connection member 1502.

In an embodiment as shown in FIG. 15, the first fixing connection member in the connection assembly is fixed to the external first support assembly by means of the fixing part. As the stabilized platform is attached to one plane of the external first support assembly, the contact area between the first fixing connection member and the first support assembly is increased. Then, when the external first support assembly rotates about the second support assembly by means of the point connection of the connection part and the second fixing connection member, the frictional force between the first fixing connection member and the first support assembly can be increased to avoid the relative movement between the first fixed connect member and the first support assembly, and therefore the generation of rotational resistance can be reduced.

In an embodiment provided by the present invention, the point connection may be in a manner that two contact components are not in full contact and the contact area is less than a predetermined value. For example, when the connection part and the second fixing connection member are connected together in a form of point connection, the contact area is less than 1 square millimeter.

Figure 16:
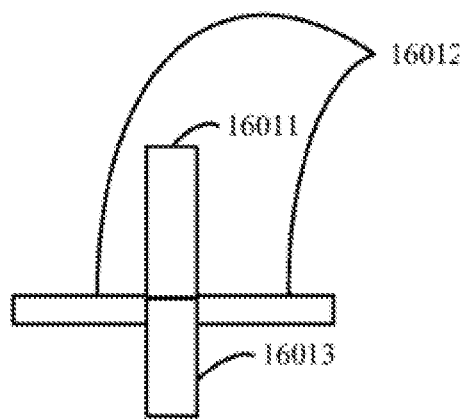
FIG. 16 is a structural schematic diagram of a first fixing connection member provided by an embodiment of the present invention.

As shown in FIG. 16, in another embodiment of the present invention, the stabilized platform 16012 and the connection part 16013 are arranged at one end of the fixing part 16011; the stabilized platform 16012 and the fixing part 16011 form a "⊥" shape; the stabilized platform 16012 and the connection part 16013 form a "⊤" shape;

a first vertical center line of the fixing part 16011 relative to the stabilized platform 16012 coincides with a second vertical center line of the connection part 16013 relative to the stabilized platform 16012. It is worth noting that the shape of the stabilized platform can be arbitrarily set such as a hexagon, a circle, and the like.

In another embodiment of the present invention, the fixing part is inserted into the first support assembly through a first plane of the external first support assembly. If a spiral is arranged in a housing of the fixing part, the fixing part is inserted into the first support assembly by means of the spiral, so that the first fixing connection member is fixed to the external first support assembly. When the fixing part is inserted into the first support assembly, the stabilized platform is attached to the first plane, and therefore, the contact area between the first fixing connection member and the external first support assembly is effectively increased. Then, as the first support assembly rotates, the frictional force between the first fixing connection member and the external first support assembly increases, such that the first fixing connection member can be fixed on the first support assembly more stably.

In another embodiment of the present invention, the connection part and the second fixing connection member may be a top cone and a jewel bearing, wherein the jewel bearing is of a cake structure. A plane of the cake structure is provided with a tapered groove. The top cone is of a tapered structure, wherein the tip of the top cone is located in the tapered groove in the jewel bearing. The top cone is connected to the jewel bearing in a form of point contact. For example, the tip of the tip cone has an area of 0.5 square millimeter, and the top cone is connected to the tapered groove of the jewel bearing in a form of point connection by means of this tip having the area of 0.5 square millimeter.

Figure 17:
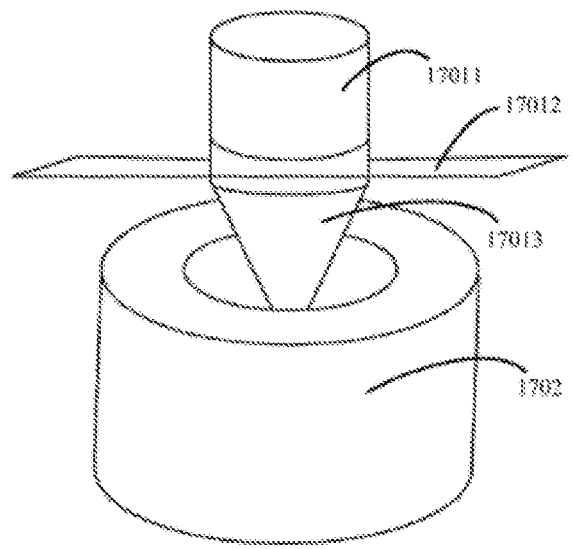
FIG. 17 is a structural schematic diagram of a connection assembly provided by another embodiment of the present invention.

The structure of the connection assembly will be described below in the following two cases:

in Case 1: when the connection part is a top cone, the second fixing connection member is a jewel bearing; as shown in FIG. 17, the fixing part 17011 and the stabilized platform 17012 form a "⊥" shape; the stabilized platform 17012 and the top cone 17013 serving as the connection part form a "⊤" shape; the tip of the top cone 17013 is in point contact with the bottom of the jewel bearing 1702 serving as the second fixing connection member, and the jewel bearing 1702 supports the top cone 17013, the stabilized platform 17012, and the fixing part 17011.

Figure 18:
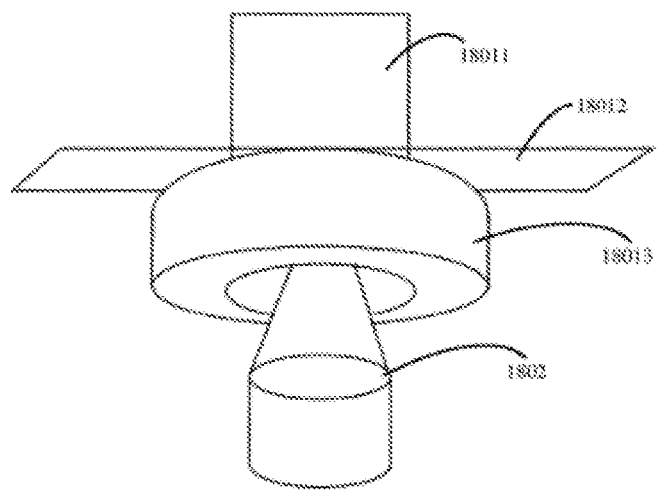
FIG. 18 is a structural schematic diagram of a connection assembly provided by another embodiment of the present invention.

In Case 2: when the connection part is a jewel bearing, the second fixing connection member is a top cone; as shown in FIG. 18, the fixing part 18011 and the stabilized platform 18012 form a "⊥" shape; the stabilized platform 18012 and the top cone 18013 serving as the connection part form a "⊤" shape; the tip of the top cone 18013 serving as the second fixing connection member is in point contact with the bottom of the jewel bearing 18013, and the jewel bearing 18013, the stabilized platform 18012, and the fixing part 18011 are fixed by the top cone 1802.

Figure 19:
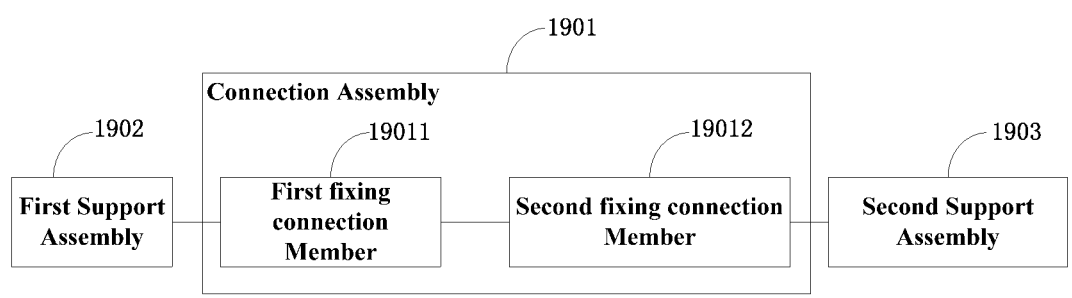
FIG. 19 is a structural schematic diagram of a support provided by an embodiment of the present invention.

As shown in FIG. 19, the embodiment of the present invention provides a support, comprising the connection assembly 1901 described above, a first support assembly 1902 and a second support assembly 1903, wherein the first support assembly 1902 is used for fixing the first fixing connection member 19011 in the connection assembly 1901, and a plane in the first support assembly 1902 is attached to the stabilized platform in the first fixing connection member 19011;

the second support assembly 1903 is used for fixing the second fixing connection member 19012 in the connection assembly 1901;

the first fixing connection member 19011 and the second fixing connection member 19012 in the connection assembly 1901 are connected together in a manner of point connection;

the first support assembly 1902 is fixedly connected to an external supported object; and the first support assembly 1902 rotates, under the driving force of the external supported object, relative to the second support assembly 1903 through the first fixing connection member 19011.

Figure 20:
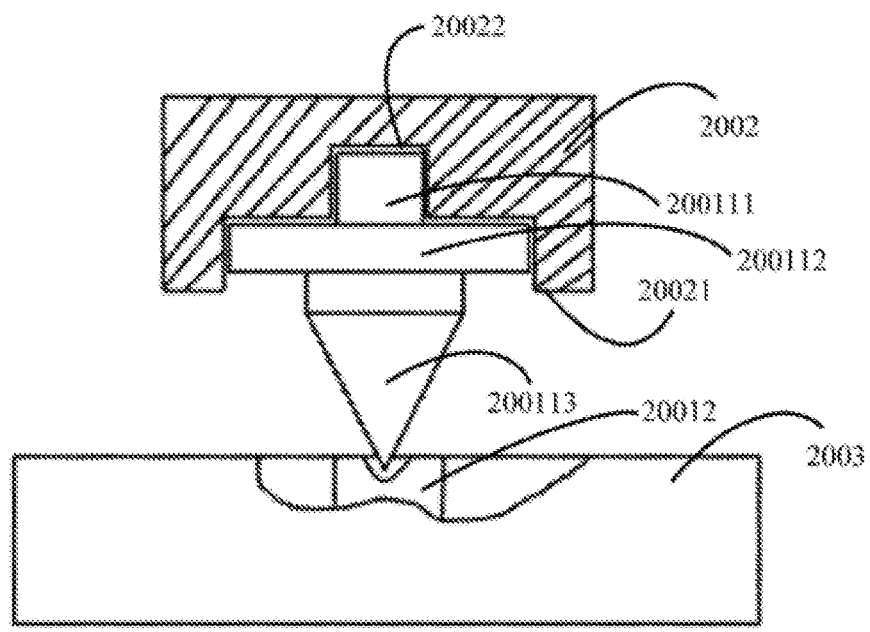
FIG. 20 is a structural schematic diagram of a support provided by another embodiment of the present invention.

In another embodiment of the present embodiment, the first support assembly comprises a concave plane and an insertion hole, wherein the insertion hole is located in a groove of the concave plane, and forms a shape "ម" together with the groove; the fixing part of the first fixing connection member is inserted into the insertion hole; the stabilized platform of the first fixing connection member is attached to the groove. In order to accurately describe this connection manner, a description will be made by taking the case that the connection part of the first fixing connection member is a top cone, and the second fixing connection member is a jewel bearing as an example. As shown in FIG. 20, the first support assembly 2002 comprises a concave plane 20021 and an insertion hole 20022, wherein the insertion hole 20022 is located in a groove of the concave plane 20021, and forms a shape "⊌" together with the groove; the fixing part 200111 of the first fixing connection member 20011 is inserted into the insertion hole 20022, the stabilized platform 200112 of the first fixing connection member 20011 is attached to the groove. The jewel bearing 20012 which serves as a second fixing connection member is fixed to the second support assembly 2003, and the top cone 200113 serves as a connection part of the first fixing connection member 20011. The tip of the top cone 200113 is located in a tapered groove in the jewel bearing 20012, and the top cone 200113 is connected to the jewel bearing 20012 in a form of point contact. By means of this connection manner, the contact area between the first fixing connection member 20011 and the first support assembly 2002 is effectively increased. Then, when the external supported object drives the first support assembly 2002 to rotate, the frictional force between the first fixing connection member 20011 and the first support assembly 2002 is greatly increased, so that the first fixing connection member 20011 can be fixed on the first support assembly 2002 more firmly, thereby reducing the rotational resistance when the first support assembly 2002 rotates relative to the second support assembly 2003.

Figure 21:
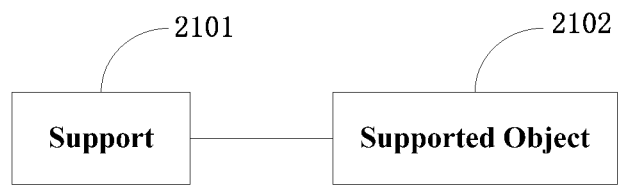
FIG. 21 is a schematic diagram of an apparatus for measuring blood coagulation data as provided by another embodiment of the present invention.

As shown in FIG. 21, an embodiment of the present invention provides an apparatus for measuring blood coagulation data, comprising any support 2101 described above and the supported object 2102, wherein the supported object 2102 is fixedly connected to the first support assembly in the support 2101, and the supported object 2102 drives, under an external power, the first support assembly to rotate.

In another embodiment of the present invention, the supported object 2102 comprises a rotary shaft, wherein the rotary shaft is fixedly connected to the first support assembly in the support; the rotary shaft drives the first support assembly to rotate under the driving force of the blood to be measured.

Figure 22:
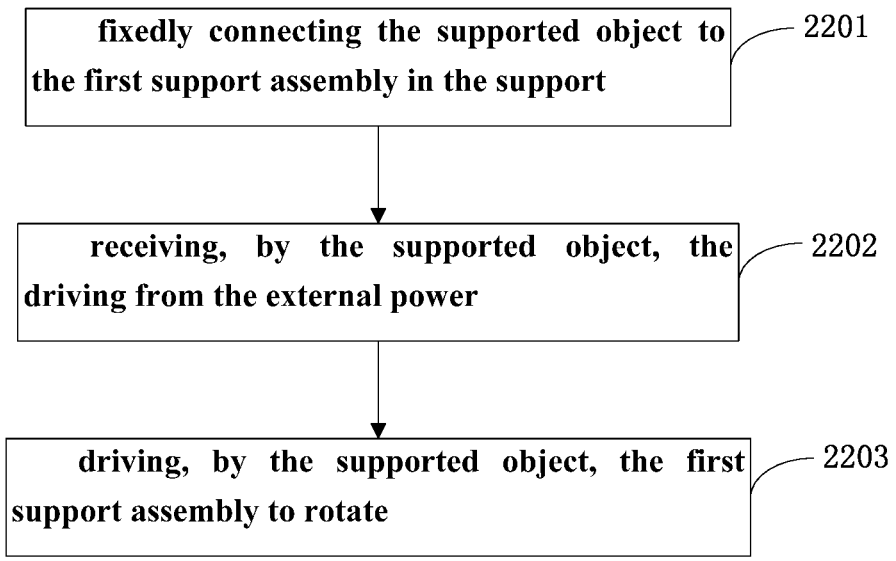
FIG. 22 is a flowchart of a use method for an apparatus for measuring blood coagulation data as provided by an embodiment of the present invention.

As shown in FIG. 22, the embodiment of the present invention provides a use method for any apparatus for measuring blood coagulation data. The use method comprises:

Operation 2201: fixedly connecting the supported object to the first support assembly in the support; Operation 2202: receiving, by the supported object, the driving from the external power; and Operation 2203: driving, by the supported object, the first support assembly to rotate.

In the above operation 2203, the supported object is fixedly connected to the first support assembly. The first support assembly is connected to the second support assembly in a form of point connection of the connection assembly. The supported object drives, under an external driving force, the first support assembly to rotate about a contact point of contact connection. Since the second support assembly supports the first support assembly and the supported object only by one contact point, the frictional force generated when the first support assembly and the second support assembly rotate relative to each other is relatively small, thereby reducing the rotational resistance when the supported object rotates.

In an embodiment of the present invention, the use method is applied to the apparatus for measuring blood coagulation data. The supported object comprises a rotary shaft. The specific implementation manner of the operation 2202 includes: placing the rotary shaft in the measured blood, and accepting driving when the measured blood rotates. That is, after the lower end of the rotary shaft is immersed in the blood to be measured by a specified length, a blood container is rotated at a certain speed by a rotating device, and the blood container rotates to drive the blood to be measured to rotate. Since the blood to be measured has a certain viscosity, the blood to be measured rotates on the rotary shaft to generate a rotational moment, and the rotary shaft rotates under the action of the rotating moment. The larger the viscosity of the blood to be measured, the larger the rotation angle of the rotary shaft.

In an embodiment of the present invention, after operation 2203, the method further comprises: providing a rotation angle by the rotary shaft. As mentioned above, since the blood to be measured has a certain viscosity, the blood to be measured rotates on the rotary shaft to generate a rotational moment, and the rotary shaft rotates under the action of the rotating moment. Then, the rotation angle of the rotary shaft is related to the viscosity of the blood to be measured. The apparatus for measuring blood coagulation data may sense the rotation angle of the rotary shaft through various sensors, form a thrombelastogram according to the rotation angle of the rotary shaft, and obtain an index parameter reflecting the elasticity of the blood to be measured according to the thrombelastogram, or directly convert the rotation angle of the rotary shaft to an index parameter that reflects the elasticity of the measured blood.

Figure 23:
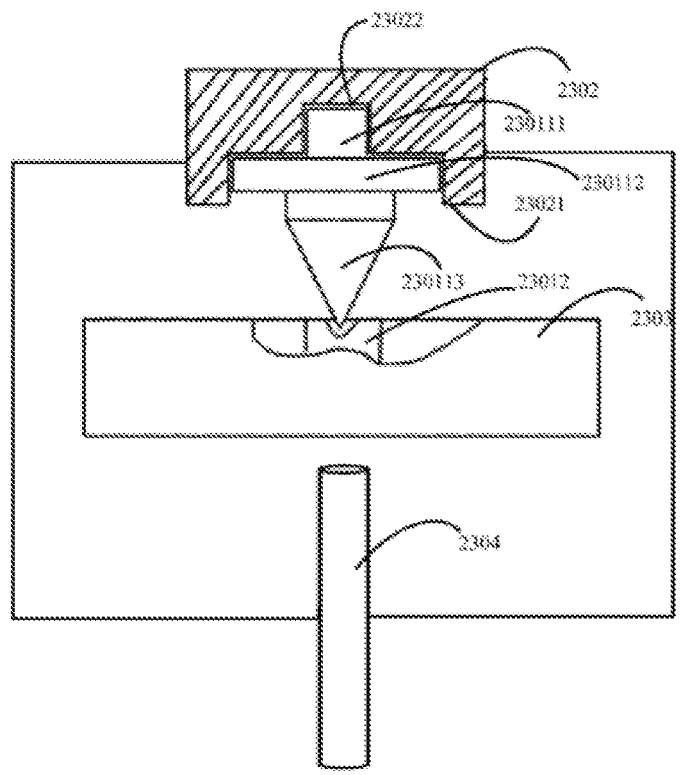
FIG. 23 is a structural schematic diagram of an apparatus for measuring blood coagulation data as provided by a further embodiment of the present invention.
Figure 24:
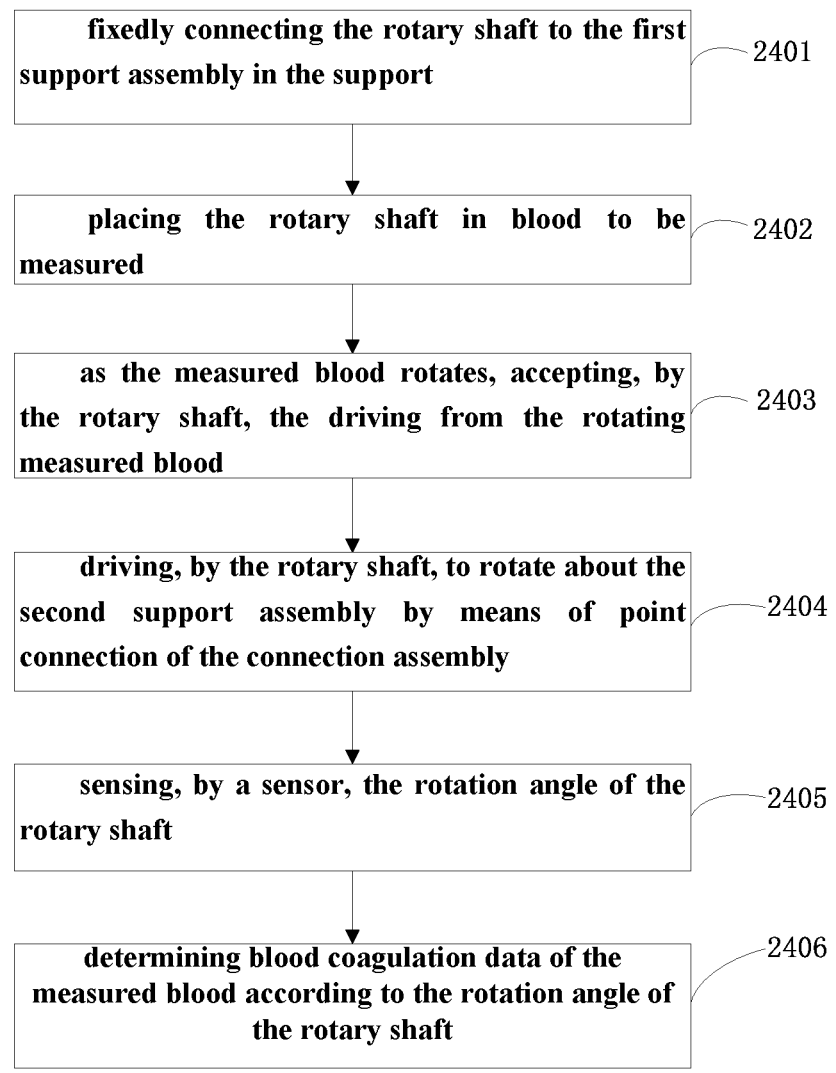
FIG. 24 is a flowchart of a use method for an apparatus for measuring blood coagulation data as provided by another embodiment of the present invention.

By taking the apparatus for measuring blood coagulation data as shown in FIG. 23 as an example, the use method for the apparatus for measuring the blood coagulation data will be described in detail. As shown in FIG. 24, the use method comprises the following steps 2401-2406.

Operation 2401: fixedly connecting the rotary shaft to the first support assembly in the support.

As shown in FIG. 23, the apparatus for measuring blood coagulation data comprises a rotary shaft 2304 and the support shown in FIG. 20, wherein a first fixing connection member 23011 (including a fixing part 230111, a stabilized platform 230112 and a top cone 230113) of the connection assembly 2301 is fixed on a first support assembly 2302, and a jewel bearing 23012 serving as a second fixing connection member is fixed on a second support assembly 2303. The first fixing connection member 23011 is fixed on the first support assembly 2302 in such a fixing manner: the fixing part 230111 is inserted into an insertion hole 23022 in the first support assembly 2302; the insertion hole 23022 is formed in a groove 23023 in a "concave" plane 23021; the stabilized platform 230112 is attached to the groove 23023, and the tip of the top cone 230113 serving as the connection part is connected to the jewel bearing 23012 in a form of point contact; the fixing part 230111, the stabilized platform 230112 and the top cone 230113 can exist as an integer, i.e., there is no connection gap among the fixing part 230111, the stabilized platform 230112 and the top cone 230113. In addition, the rotary shaft 2304 is connected to the first support assembly 2302, wherein the connection manner can be flexibly set as long as the rotary shaft 2304 is kept perpendicular. For example, the first support assembly 2302 may be set to a "square" shape, and the first fixing connection member 23011 is mounted on the inner side of the upper end of the "square" shape; the rotary shaft 2304 is mounted on the outer side of the lower end of the "square" shape, and the second support assembly 2303 passes through the "square" shape and is connected to the tip of the top cone 230113 on the first fixing connection member 23011 on the inner side of the upper end of the "square" shape.

Operation 2402: placing the rotary shaft in blood to be measured.

In this step, the blood to be measured may be contained in a blood container, and the rotary shaft 2304 may be driven, under a certain acting force, into the blood container by a lift in the apparatus for measuring blood coagulation data, such that the rotary shaft 2304 is immersed into the blood to be measured by a specified length.

Operation 2403: as the measured blood rotates, accepting, by the rotary shaft, the driving from the rotating measured blood.

After the lower end of the rotary shaft 2304 is immersed into the measured blood by a specified length, the blood container rotates at a certain speed by the rotating device in the apparatus for measuring the blood coagulation data, and the blood container rotates to drive the measured blood to rotate. Since the blood to be measured has a certain viscosity, the blood to be measured rotates on the rotary shaft 2304 to generate a rotational moment, and the rotary shaft 2304 rotates under the rotating moment. The larger the viscosity of the measured blood, the larger the rotation angle of the rotary shaft 2304.

Operation 2404: driving, by the rotary shaft, to rotate about the second support assembly by means of point connection of the connection assembly.

Since the rotary shaft 2304 is fixedly connected to the first support assembly 2302, when the rotary shaft 2304 rotates, the top cone 230113 of the first fixing connection member 23011 fixed by the first support assembly 2302 rotates at the same angle with the rotary shaft 2304 about the jewel bearing 23012 by means of a connection point with the jewel bearing 23012. The second support assembly 2303 supports the rotary shaft 2304 and the first support assembly 2302 by means of the jewel bearing 23012 and the top cone 230113. Due to the single point contact between the jewel bearing 23012 and the top cone 230113, the frictional force generated when the jewel bearing 23012 and the top cone 230113 rotate relative to each other is small, thereby reducing the rotational resistance of the support on the rotary shaft when the rotary shaft 2304 rotates.

Operation 2405: sensing, by a sensor, the rotation angle of the rotary shaft.

Operation 2406: determining blood coagulation data of the measured blood according to the rotation angle of the rotary shaft.

The specific process of Operation 2405 and Operation 2406 includes: sensing the rotation angle of the rotary shaft through various sensors, forming a thrombelastogram according to the rotation angle of the rotary shaft, and acquiring an index parameter reflecting the elasticity o the measured blood according to the thrombelastogram, or directly converting the rotation angle of the rotary shaft to an index parameter that reflects the elasticity of the measured blood.

Various embodiments provided by the present invention have the following beneficial effects:

1. In the embodiment of the present invention, the blood cup support may drive, under the first driving force, the blood cup that is not used and the lid of the blood cup to ascend, and connect the lid of the blood cup and the rotary shaft, and therefore, the ascending of the blood cup and the mounting of the lid of the blood cup are automatically completed before the blood coagulation data is measured. The blood cup support may drive, under the second driving force, the blood cup that is used to descend, the detachment mechanism may separate the lid of the used blood cup from the rotary shaft under the second driving force at the same time, and therefore the descending of the blood cup and the detachment of the lid of the blood cup are automatically completed after the blood coagulation data is measured. In this way, in the process of measuring the blood coagulation data, the apparatus for measuring the blood coagulation data automatically completes the ascending and descending of the blood cup as well as the mounting and detachment of the lid of the blood cup, instead of a manner of manual operation. Therefore, the labor intensity of the blood coagulation data is reduced.

2. In the embodiment of the present invention, the blood cup support and the detachment mechanism are driven by means of the stepping motor and the screw. Since the stepping motor may rotate forwardly or reversely and has relatively high control precision, and meanwhile the screw also has relatively high travel control precision while transmitting power, the travel precision of the blood cup support and the detachment mechanism can be improved by driving the blood cup support and the detachment mechanism by means of the stepping motor and the screw, thereby ensuring that the blood cup and the lid of the blood cup can be mounted in place and can be detached smoothly.

3. In the embodiment of the present invention, the bottom of the blood cup support is provided with a through hole into which the thimble can extend. When the blood cup support descends, the thimble may eject the blood cup out from the blood cup support, thereby realizing automatic detachment of the blood cup. The blood cup can be detached, without manual operation, thereby reducing the labor intensity in blood coagulation data measurement.

4. In the embodiment of the present invention, the position of the rotary shaft is fixed by the limiting mechanism when the blood cup and the lid of the blood cup are mounted or detached, such that the bearing of the rotary shaft can be prevented from being damaged when the blood cup and the lid of the blood cup are mounted or detached, and the rotary shaft can be prevented from deforming. Therefore, the safety of the apparatus for measuring the blood coagulation data and the accuracy in blood coagulation data measurement are improved.

5. In the embodiment of the present invention, the jewel bearing is connected to the first support, and the top cone and the rotary shaft are connected to the second support respectively, and the first support supports the second support and the rotary shaft by the jewel bearing and the top cone which are matched together. When it is necessary to connect the lid of the blood cup to the rotary shaft or to separate the lid of the blood cup from the rotary shaft, the positions of the jewel bearing and the top cone are limited by the limiting mechanism to separate the jewel bearing from the top cone, and then the lid of the blood cup is connected to the rotary shaft or separated from the rotary shaft. In this way, when the lid of the blood cup is connected to or separated from the rotary shaft, the jewel bearing is not in contact with the top cone, such that the force encountered by the rotary shaft cannot act on the jewel bearing to prevent the jewel bearing from being damaged when the lid of the blood cup is connected to or separated from the rotary shaft, thereby reducing the risk that the jewel bearing is damaged.

6. In the embodiment of the present invention, there are a plurality of implementation manners for separating the jewel bearing from the top cone, wherein the second support may be driven to cause the second support to drive the top cone to ascend to separate the top cone from the jewel bearing; the first support may also be driven to cause the first support to drive the jewel bearing to descend, and at the same time, the position of the second support is limited by the limiting mechanism to achieve of the effect of separating the top cone from the jewel bearing. In this way, the separation of the top cone from the jewel bearing can be achieved by different mechanism forms, and therefore the applicability of the apparatus for measuring blood coagulation data is improved.

7. In the embodiment of the present invention, the apparatus for measuring blood coagulation data may further comprise the detachment mechanism. By means of the detachment mechanism, the lid of the blood cup can be detached from the rotary shaft under a driving force. In this way, as the device such as the stepping motor drives the detachment mechanism, the lid of the blood cup can be automatically separated from the rotary shaft; the lid of the blood cup can be removed from the rotary shaft, without manual operation, thereby reducing the labor intensity of the measurement person during the blood coagulation data measurement.

8. In the embodiment of the present invention, the top cone and the second support are respectively provided with the guide platform respectively. After the top cone is connected to the second support by threads, the guide platform on the top cone is attached to the guide platform on the second support, thereby ensuring that an included angle between the top cone and the second support is a right angle, avoiding the influence of the inclination of the rotary shaft on the measured blood coagulation data and improving the accuracy of measuring the blood coagulation data by the apparatus for measuring the blood coagulation data.

9. In the embodiment of the present invention, the first magnet and the second magnet whose like magnetic poles are opposite are arranged on the first support and the second support. Due to the repulsive force between the first magnet and the second magnet, the acting force between the top cone and the jewel bearing may be reduced, thereby reducing the frictional force between the top cone and the jewel bearing, such that the rotation angle of the rotary shaft may reflect the viscosity information of the blood to be measured more really, and further the accuracy of measuring the blood coagulation data by the apparatus for measuring blood coagulation data is improved.

10. In the embodiment of the present invention, the first fixing connection member in the connection assembly is fixed to the external first support assembly by means of the fixing part. As the stabilized platform is attached to one plane of the external first support assembly, the contact area between the first fixing connection member and the first support assembly is increased. Then, when the external first support assembly rotates about the second support assembly through the point connection of the connection part and the second fixing connection member, the frictional force between the first fixing connection member and the first support assembly can be increased to avoid the relative movement between the fixed connect member and the first support assembly, and therefore the generation of rotational resistance can be reduced.

11. In the embodiment of the present invention, the first fixing connection member in the connection assembly is connected to the second fixing connection member in a form of point connection. When the first fixing connection member is fixed to the first support assembly and the second fixing connection member is fixed to the second support assembly respectively, the process of driving, by the supported object that is in stress, the first support assembly to rotate about the second support assembly is actually a point connection rotation between the first fixing connection member and the second fixing connection member. Then, when the first support assembly and the second support assembly rotate relative to each other, only one contact point generates a frictional force. This embodiment can reduce the generation of the rotational frictional force compared with the prior art structure including a plurality of contact points for generating frictional force. Therefore, the rotational resistance encountered when the supported object rotates is reduced.

12. In the embodiment of the present invention, the connection part in the first fixing connection member and the second connection member, which are included in the connection assembly, may be the jewel bearing and the top cone, wherein the tip of the top cone is located in the tapered groove of the jewel bearing, and the tip of the top cone is in point contact with the bottom of the tapered groove. Due to the high hardness of the jewel bearing, the frictional force generated by the jewel bearing and the top cone which rotate relative to each other is relatively small, so that the rotational resistance can be further reduced. When the connection assembly is applied to the apparatus for measuring blood coagulation data, the sensitivity of the apparatus for measuring blood coagulation data and the measurement accuracy can be improved.

13. In the embodiment of the present invention, the connection part in the first fixing connection member of the connection assembly may be the jewel bearing or the top cone, which may be flexibly selected according to the structure and functions of actual devices, so that the connection assembly has a certain applicability.

It can be appreciated that, while the terms "first", "second" and so on may be used herein to distinguish one entity or operation from another, it does not require or imply such a relation or sequence between these entities or operations. Further, the terms "include", "comprise" or any variation thereof are intended to cover an nonexclusive containing, such that a process, a method, an item or a device containing a series of elements not only includes these elements, but also includes other elements that are not set forth specifically, or also includes an inherent element of such a process, method, item or device. Without further limitation, an element defined by a phrase "include a" does not mean that other elements are excluded from the process, method, item or device.

Aspects

The various aspects numbered below further provide the disclosure of the present invention. It should be noted that any of the following aspects 1-6 may be combined with any of the aspects 7-10, may also be combined with any of the aspects 11-16, may also be combined with any of aspects 17-20, may also be combined with any of aspects 21-24, and may also be combined with any of aspects 25-26, may also be combined with any of the aspects 27-30, may also be combined with any of the aspects 31-34, and may also be combined with any of the aspects 35-37. Moreover, any of the following aspects 7-10 may be combined with any of the aspects 11-16, may also be combined with any of aspects 17-20, may also be combined with any of aspects 21-24, may also be combined with any of aspects 25-26, and may also be combined with any of the aspects 27-30, may also be combined with any of the aspects 31-34, and may also be combined with any of the aspects 35-37. Any of the following aspects 11-16 may be combined with any of the aspects 17-20, may also be combined with any of aspects 21-24, may also be combined with any of aspects 25-26, may also be combined with any of aspects 27-30, and may also be combined with any of aspects 31-34, and may also be combined with any of aspects 35-37. Any of the following aspects 17-20 may be combined with any of the aspects 21-24, may also be combined with any of aspects 25-26, may also be combined with any of aspects 27-30, may also be combined with any of aspects 31-34, and may also be combined with any of aspects 35-37. Any of the following aspects 21-24 may be combined with any of aspects 25-26, may also be combined with any of aspects 27-30, may also be combined with any of aspects 31-34, and may also be combined with any of aspects 35-37. Any of the following aspects 25-26 may be combined with any of aspects 27-30, may also be combined with any of aspects 31-34, and may also be combined with any of aspects 35-37. Any of the following aspects 27-30 may be combined with any of aspects 31-34, and may also be combined with any of aspects 35-37. Any of the following aspects 31-34 may be combined with any of aspects 35-37.

1. An apparatus for measuring blood coagulation data, in which blood to be measured is contained in a blood cup and a lid of the blood cup, comprising a blood cup support, a detachment mechanism, and a rotary shaft, wherein the blood cup support is used for supporting the blood cup that is not used and the lid of the blood cup, driving, under a first driving force, the blood cup that is not used and the lid of the blood cup to ascend until the lid of the unused blood cup is connected to the rotary shaft, and driving, under a second driving force, a blood cup that is used to descend; and the detachment mechanism is used for separating, under the second driving force, the lid of the used blood cup from the rotary shaft.

2. The apparatus according to aspect 1, further comprising a screw and a stepping motor, wherein the screw comprises a screw rod and a nut, wherein the screw rod is connected to the stepping motor, and the nut is connected to the blood cup support and the detachment mechanism respectively;

the stepping motor is used for driving the screw rod, such that the screw rod rotates forwardly or reversely;

the nut is used for applying a first driving force to the blood cup support according to a rotation direction of the screw rod when the screw rod rotates forwardly, and applying a second driving force to the blood cup support and the detachment mechanism when the screw rod rotates reversely.

3. The apparatus according to aspect 1, wherein the detachment mechanism is of a flaky structure provided with a through hole in the middle;

the rotary shaft passes through the through hole in the middle of the detachment mechanism and is not in contact with the detachment mechanism; and the detachment mechanism is used for moving towards the end part of the rotary shaft under the second driving force, separating the lid of the used blood cup, which is connected to the end part of the rotary shaft, from the rotary shaft in an interference manner, and enabling the lid of the used blood cup, which is separated from the rotary shaft to fall onto the used blood cup.

4. The apparatus according to aspect 1, wherein the blood cup support is of a cup-shaped structure;

the blood cup support is used for driving, under the first driving force, the unused blood cup and the lid of the blood cup to ascend till the lid of the unused blood cup continues to ascend by a predetermined distance after contacting the rotary shaft and is connected with the unused blood cup in an interference manner, such that the rotary shaft is connected to the lid of the unused blood cup in an interference manner.

5. The apparatus according to aspect 4, further comprising a thimble, wherein a through hole is formed in the bottom of the blood cup support which is of the cup-shaped structure and allows the fixed thimble to pass through;

the thimble is used for contacting the bottom of the used blood cup after the blood cup support drives the used blood cup to descend by a set distance, and separating the blood cup support and the used blood cup which are connected in an interference manner when the blood cup support continues to descend.

6. The apparatus according to any one of aspects 1 to 5, further comprising a limiting mechanism, wherein the limiting mechanism is used for fixing the position of the rotary shaft when the lid of the unused blood cup is connected to the rotary shaft, and fixing the position of the rotary shaft when the lid of the used blood cup is separated from the rotary shaft.

7. A method for mounting the blood cup based on the apparatus for measuring blood coagulation data according to any of aspects 1 to 6, comprising:

supporting, by the blood cup support, the blood cup that is not used and the lid of the blood cup; and driving, under a first driving force, the blood cup support, wherein the blood cup support moves to drive the unused blood cup and the lid of the blood cup to ascend, such that the lid of the unused blood cup is connected to the rotary shaft.

8. The method according to aspect 7, wherein the operation of driving, under a first driving force, the blood cup support, wherein the blood cup support moves to drive the unused blood cup and the lid of the blood cup to ascend till the lid of the unused blood cup is connected to the rotary shaft includes:

driving, under the first driving force, the blood cup support, wherein the blood cup support drives the unused blood cup and the lid of the blood cup to ascend till the lid of the unused blood cup continues to ascend by a set distance after contacting the rotary shaft and is connected to the unused blood cup in an interference manner, such that the rotary shaft is connected to the lid of the unused blood cup in an interference manner 9. A method for detaching the blood cup based on the apparatus for measuring blood coagulation data according to any one of aspects 1 to 6, comprising:

driving, under the second driving force, the blood cup support, wherein the blood cup support moves to drive the used blood cup to descend; and driving, under the second driving force, the detachment mechanism, wherein the detachment mechanism moves to separate the lid of the used blood cup from the rotary shaft.

10. The method according to aspect 9, wherein the operation of driving, under the second driving force, the detachment mechanism, wherein the detachment mechanism moves to separate the lid of the used blood cup from the rotary shaft includes:

driving, under the second driving force, the detachment mechanism to move towards the end part of the rotary shaft, wherein the detachment mechanism separates the lid of the used blood cup, which is connected to the end part of the rotary shaft in an interference manner, from the rotary shaft, and enabling the lid of the used blood cup, which is separated from the rotary shaft, fall into the used blood cup; and/or when the apparatus for measuring blood coagulation data comprises a thimble, the operation that the blood cup support moves to drive the used blood cup to descend includes:

after the blood cup support drives the used blood cup to descend by a set distance, enabling the thimble to be in contact with the bottom of the used blood cup, and separating the blood cup support and the used blood cup, which are connected in an interference manner when the blood cup support continues to descend.

11. An apparatus for measuring blood coagulation data, comprising a first support, a second support, a jewel bearing, a top cone, a rotary shaft and a limiting mechanism, wherein the first support is connected to the jewel bearing, and the second support is connected to the top cone and the rotary shaft respectively;

the jewel bearing is used for supporting the top cone, such that the second support and the rotary shaft are able to rotate under the driving force of the blood to be measured; and the limiting mechanism is used for limiting the positions of the jewel bearing and the top cone to separate the jewel bearing from the top cone when the lid of the external blood cup is connected to or separated from the rotary shaft.

12. The apparatus according to aspect 11, further comprising a first driving mechanism, wherein the first driving mechanism is connected to the limiting mechanism;

the first driving mechanism is used for driving the limiting mechanism when the lid of the blood cup is connected to or separated from the rotary shaft; and the limiting mechanism is used for driving the first support to move under the driving force of the first driving mechanism, such that the jewel bearing is separated from the top cone, and supporting the first support after the jewel bearing is separated from the top cone.

13. The apparatus according to aspect 11, further comprising a second driving mechanism, wherein the second driving mechanism is connected to the first support; the limiting mechanism is fixedly arranged relative to the first support and the second support;

the second driving mechanism is used for driving the first support when the lid of the blood cup is connected to or separated from the rotary shaft, such that the first support descends, and supporting the first support after the jewel bearing is separated from the top cone; and the limiting mechanism is used for limiting the position of the second support when the first support descends, such that the jewel bearing is separated from the top cone.

14. The apparatus according to aspect 11, further comprising a detachment mechanism, wherein a through hole is formed in the middle of the detachment mechanism; the rotary shaft passes through the through hole in the middle of the detachment mechanism and is not in contact with the detachment mechanism; and the detachment mechanism is used for moving towards the end part of the rotary shaft under a driving force, driving the lid of the blood cup, which is connected to the end part of the rotary shaft, to move relative to the rotary shaft, and removing the lid of the blood cup from the rotary shaft, such that the lid of the blood cup is separated from the rotary shaft.

15. The apparatus according to aspect 11, wherein a connection bolt and a first guide platform are arranged on the top cone;

a connection nut and a second guide platform are arranged on the second support;

the connection bolt is matched with the connection nut till the top cone is connected to the second support; and the first guide platform is attached to the second guide platform to limit an included angle between the top cone and the second support.

16. The apparatus according to aspect 11, further comprising a first magnet and a second magnet, wherein the first magnet is connected to the first support, and the second magnet is connected to the second support; and like magnetic poles of the first magnet and the second magnet are opposite.

17. A method for detaching a lid of a blood cup based on the apparatus for measuring blood coagulation data according to any of aspects 11 to 16, comprising:

Limiting, by the limiting mechanism, the positions of the jewel bearing and the top cone, such that the jewel bearing is separated from the top cone; and connecting or separating the lid of the blood cup to or from the rotary shaft.

18. The method according to aspect 17, when the apparatus for measuring blood coagulation data comprises the first driving mechanism, the operation of limiting the position of the first support by the limiting mechanism till the jewel bearing is separated from the top cone includes:

driving the limiting mechanism by the first driving mechanism, such that the limiting mechanism drives the first support to move, and then the jewel bearing is separated from the cone top; and after the jewel bearing is separated from the first support, the method further comprises:

supporting the first bearing by the limiting mechanism.

19. The method according to aspect 17, when the apparatus for measuring blood coagulation data comprises a second driving mechanism, the operation of limiting the position of the first support by the limiting mechanism till the jewel bearing is separated from the top cone includes:

driving the first support by the second driving mechanism, such that the first support descends; limiting the position of the second support by the limiting mechanism when the first support descends, such that the jewel bearing is separated from the top cone; and after the jewel bearing is separated from the top cone, the method further includes:

supporting the first support by the second driving mechanism.

20. The method according to aspect 17, when the apparatus for measuring the blood coagulation data comprises the detachment mechanism, the operation of separating the lid of the blood cup from the rotary shaft includes:

moving, under a driving force, the detachment mechanism to move towards the end part of the rotary shaft, such that the detachment mechanism drives the lid of the blood cup, which is connected to the end part of the rotary shaft, to move relative to the rotary shaft, removing the lid of the blood cup from the rotary shaft, and then separating the lid of the blood cup from the rotary shaft.

21. A connection assembly, comprising a first fixing connection member and a second fixing connection member, wherein the first fixing connection member comprises a fixing part, a stabilized platform fixed on the fixing part, and a connection part fixed on the fixing part, wherein the fixing part is fixed to an external first support assembly; the stabilized platform is attached to a plane of the external first support assembly;

the connection part and the second fixing connection member are connected together in a form of point connection;

the second fixing connection member is fixedly connected to an external second support assembly; and the external first support assembly rotates, under an external power, relative to the external second support assembly by means of the point connection of the connection part and the second fixing connection member.

22. The connection assembly according to aspect 21, wherein the stabilized platform and the connection part are arranged at one end of the fixing part;

the stabilized platform and the fixing part form a "⊥" shape; the stabilized platform and the connection part form a "T" shape; a first vertical center line of the fixing part relative to the stabilized platform coincides with a second vertical center line of the connection part relative to the stabilized platform.

23. The connection assembly according to aspect 21, wherein the fixing part is inserted into the first support assembly by means a plane of the external first support assembly; the stabilized platform is attached to the first plane.

24. The connection assembly according to any one of aspects 21 to 23, wherein the connection part comprises a jewel bearing, and the second fixing connection member comprises a top cone;

or the connection part comprises a top cone, and the second fixing connection member comprises a jewel bearing; wherein the jewel bearing may be of a cake structure; a tapered groove is formed in a plane of the cake structure; the top cone may be of a tapered structure, and the tip of the top cone is located in the tapered groove in the jewel bearing; the top cone is connected to the jewel bearing in a form of point contact.

25. A support, comprising the connection assembly according to any one of claims 21 to 24, a first support assembly and a second support assembly, wherein the first support assembly is used for fixing the first fixing connection member in the connection assembly, and a plane in the first support assembly is attached to the stabilized platform in the first fixing connection member;

the second support assembly is used for fixing the second fixing connection member in the connection assembly;

the first fixing connection member and the second fixing connection member in the connection assembly are connected together in a form of point connection;

the first support assembly is fixedly connected to a supported object; and the first support assembly rotates, under the driving force of the supported object, relative to the second support assembly through the first fixing connection member.

26. The support according to aspect 25, wherein the first support assembly comprises a concave plane and an insertion hole, wherein the insertion hole is located in a groove of the concave plane, and forms a shape "中" together with the groove; and the fixing part of the first fixing connection member is inserted into the insertion hole, and the stabilized platform of the first fixing connection member is attached to the groove.

27. The apparatus for measuring blood coagulation data, comprising the support according to aspect 25 or 26 and a supported object, wherein the supported object is fixedly connected to the first support assembly in the support, and the supported object drives, under an external power, the first support assembly to rotate.

28. The apparatus according to aspect 27, which is applied to the apparatus for measuring blood coagulation data, wherein the supported object comprises a rotary shaft, wherein the rotary shaft is fixedly connected to the first support assembly in the support; and the rotary shaft drives, under the driving force of measured blood, to rotate the first support assembly.

29. A use method for the apparatus for measuring blood coagulation data according to aspect 27 or 28, comprising:

fixedly connecting the supported object to the first support assembly in the support;

accepting, by the supported object, the driving from the external power; and driving, by the supported object, the first support assembly to rotate.

30. The use method according to aspect 29, which is applied to the apparatus for measuring blood coagulation data, wherein the supported object comprises a rotary shaft; wherein the operation of accepting, by the supported object, the driving from the external power includes: placing the rotary shaft in the measured blood, and accepting driving when the measured blood rotates;

and/or after the supported object drives the first support assembly to rotate, the method further comprises: providing a rotation angle by the rotary shaft.

31. A system for measuring blood coagulation data, comprising an apparatus for measuring blood coagulation data and a blood cup, wherein the blood cup is used for containing measured blood; and the apparatus for measuring blood coagulation data is used for performing blood coagulation analysis on blood in the blood cup.

32. The system according to aspect 31, the blood cup comprises: a container for containing liquid;

at least one heater which is in contact with the container and used for heating the liquid in the container; and a temperature controller which is connected to the at least one heater, and used for acquiring a current temperature of each heater and performing heating control on each heater according to the current temperature of each heater and a pre-stored set temperature.

33. The system according to aspect 32, wherein the temperature controller comprises:

at least one temperature sensor which is connected to the at least one heater in a one-to-one correspondence manner, and used for acquiring a current temperature of the heater connected thereto, and outputting the acquired current temperature of each heater to a comparator; and the comparator which is connected to the at least one temperature sensor and at least one heater, and used for performing heating control on each heater according to the current temperature of each heater and the pre-stored set temperature.

34. The system according to aspect 33, wherein the temperature sensor comprises a thermistor which is used for outputting a current resistance value to a signal converter according to the current temperature of the heater connected to the temperature sensor; and the temperature controller further comprises the signal converter which is connected to the thermistor and the comparator and is used for outputting the current temperature of each heater to the comparator according to the current resistance value outputted by each thermistor.

35. An apparatus for measuring blood coagulation data, comprising a support, a rotary shaft and a position correction device, wherein the support is connected to one end of the rotary shaft and used for supporting the rotary shaft, such that the other end of the rotary shaft is placed in the external measured blood;

the rotary shaft rotates under the driving force of the measured blood; and the position correction device is connected to the rotary shaft and is used for, when the rotary shaft rotates away from a balanced position, generating an acting force for rotating the rotary shaft towards the balanced position.

36. The apparatus according to aspect 35, wherein the position correction device comprises at least one hair spring;

an inner ring of each hair spring is fixedly connected to an outer circumferential surface of the rotary shaft; and an outer ring of each hair spring is fixedly connected to the support.

37. The apparatus according to aspect 36, wherein when the position correction device comprises at least two hair springs, the spiral direction of at least one hair spring in the at least two hair springs from the inner ring to the outer ring is opposite to the spiral direction of the other hair spring from the inner ring to the outer ring.

The present invention may be implemented in other forms without departing from the spirit and novel characteristics of the present invention. Various embodiments disclosed in the present application should be considered in all aspects in an illustrative manner, rather than a restrictive manner. The scope of the present invention is claimed by the appended aspects rather than by the foregoing description; all modifications made within equivalent meaning and equivalent scope of the various aspects are intended to be included within the protection scope of the present invention.

The invention claimed is:

1. An apparatus for measuring blood coagulation data, in which blood to be measured is contained in a cup and a lid of the cup, comprising:
 a rotary shaft;
 a cup support having a cup-shaped structure and configured to:
  support the cup prior to containing blood,
  drive, under a first driving force, the cup prior to containing the blood and the lid to ascend until the lid connects to an end part of the rotary shaft in an interference manner, and
  drive, under a second driving force, the cup containing the blood to descend;
 a detachment mechanism having a structure provided with a through hole, the rotary shaft passing through the through hole of the detachment mechanism and is not in contact with the detachment mechanism, and the detachment mechanism being configured to move, under the second driving force, towards the end part of the rotary shaft, separating the lid from the rotary shaft, and enabling the lid of the cup, which is separated from the rotary shaft, to fall onto the cup containing the blood; and
 a thimble configured to contact the bottom of the cup containing the blood after the cup support drives the cup containing the blood to descend by a set distance, and to separate the cup support and the containing the blood, wherein
 a through hole is formed in the bottom of the cup support and allows the thimble to pass through the through hole when the cup containing the blood is descended by the set distance.

2. The apparatus according to claim 1, further comprising:
 a power source and a transmission mechanism, wherein
 the power source is configured to supply a driving force to the transmission mechanism, and
 the transmission mechanism is configured to apply the first driving force to the cup support under a driving force of the power source, and to apply the second driving force to the cup support and the detachment mechanism.

3. The apparatus according to claim 2, wherein
 the power source comprises a stepping motor, and the transmission mechanism comprises a screw,
 the screw comprises a screw rod connected to the stepping motor, and a nut connected to the cup support and the detachment mechanism respectively,
 the stepping motor is configured to drive the screw rod, such that the screw rod rotates forwardly or reversely, and
 the nut is configured to apply the first driving force to the cup support when the screw rod rotates forwardly, and to apply the second driving force to the cup support and the detachment mechanism when the screw rod rotates reversely.

4. The apparatus according to claim 1, wherein
 the cup support is configured to drive the cup prior to containing the blood and the lid to ascend under the first driving force until the lid contacts the rotary shaft and to ascend by a predetermined distance after contacting the rotary shaft, so as to connect the cup prior to containing the blood and the cup support in an interference manner and to connect the end part of the rotary shaft and the lid in the interference manner.

5. The apparatus according to claim 1, wherein the detachment mechanism has a planar structure provided with the through hole.

6. The apparatus according to claim 1, wherein the detachment mechanism is configured to move, under the second driving force, towards the end part of the rotary shaft by descending towards the end part of the rotary shaft.

7. The apparatus according to claim 1, wherein the cup support rotates about a central axis, and in turn rotates the cup when in use.

* * * * *